US008906661B2

(12) United States Patent
Soejima

(10) Patent No.: US 8,906,661 B2
(45) Date of Patent: Dec. 9, 2014

(54) ADAMTS-13 MUTANT

(71) Applicant: The Chemo-Sero-Therapeutic Research Institute, Kumamoto (JP)

(72) Inventor: Kenji Soejima, Kikuch (JP)

(73) Assignee: The Chemo-Sero-Therapeutic Research Institute, Kumamoto-shi (JP)

( * ) Notice: Subject to any disclaimer, the term of this patent is extended or adjusted under 35 U.S.C. 154(b) by 0 days.

(21) Appl. No.: 14/166,177

(22) Filed: Jan. 28, 2014

(65) Prior Publication Data

US 2014/0193881 A1  Jul. 10, 2014

Related U.S. Application Data

(62) Division of application No. 12/666,051, filed as application No. PCT/JP2008/061211 on Jun. 19, 2008, now Pat. No. 8,685,665.

(30) Foreign Application Priority Data

| Jun. 22, 2007 | (JP) | 2007-164531 |
| Jan. 31, 2008 | (JP) | 2008-020012 |
| Jan. 31, 2008 | (JP) | 2008-020177 |

(51) Int. Cl.
| C12N 9/48 | (2006.01) |
| C07H 21/04 | (2006.01) |
| C12N 9/64 | (2006.01) |
| A61K 38/00 | (2006.01) |

(52) U.S. Cl.
CPC ............... *C12N 9/6489* (2013.01); *A61K 38/00* (2013.01)
USPC .......................................... 435/212; 536/23.2

(58) Field of Classification Search
CPC .............................. C12N 9/6489; A61K 38/00
USPC .......................................... 435/212; 536/23.2
See application file for complete search history.

(56) References Cited

U.S. PATENT DOCUMENTS 7,575,872 B2  8/2009  Soejima et al.

FOREIGN PATENT DOCUMENTS

| EP | 1 609 804 | 12/2005 |
| JP | 2007-248395 | 9/2007 |
| WO | WO 02/088366 A1 | 11/2002 |
| WO | WO 03/016492 | 2/2003 |
| WO | WO 2004/029242 A1 | 4/2004 |
| WO | WO 2004/083250 A1 | 9/2004 |
| WO | WO 2005/062054 A1 | 7/2005 |

OTHER PUBLICATIONS

Kenji Soejima, "VWF Setsudan Koso (ADAMTS13) no Kozo to Kino", Structure and function Relationships of ADAMTS 13, Separate Volume Igaku no Ayumi, Ketsueki Shikkan-State of Arts, Ver. 3, 2005, pp. 143-146 (with English abstract).

Kim L. Morrison, et al., "Combinatorial Alanine-Scanning", Current Opinion in Chemical Biology, vol. 5, No. 3, 2001, pp. 302-307.

Kenji Soejima, et al. "A Novel Human Metalloprotease Synthesized in the Liver and Secreted into the Blood: Possibly, the von Willebrand Factor-Cleaving Protease?", The Japanese Biochemical Society, vol. 130, No. 4, 2001, pp. 475-480.

Kenji Soejima, et al., "Interplay Between ADAMTS13 and von Willebrand Factor in Inherited and Acquired Thrombotic Microangiopathies", Seminars in Hematology, vol. 42, 2005, pp. 56-62.

Patricia J. Anderson, et al., "Zinc and Calcium Ions Cooperatively Modulate ADAMTS13 Activity", Journal of Biological Chemistry, vol. 281, No. 2, Jan. 13, 2006, pp. 850-857.

Tomoko Ono, et al., "Severe secondary deficiency of von Willebrand factor-cleaving protease (ADAMTS13) in patients with sepsis-induced disseminated intravascular coagulation: its correlation with development of renal failure", Blood, vol. 107, No. 2, 2006, pp. 528-534.

Aubrey Bernardo, et al., "Effects of inflammatory cytokines on the release and cleavage of the endothelial cell-derived ultralarge von Willebrand factor multimers under flow", Blood, vol. 104, No. 1, Jul. 1, 2004, pp. 100-106.

Leticia H. Nolasco, et al, "Hemolytic uremic syndrome-associated Shiga toxins promote endothelial-cell secretion and impair ADAMTS13 cleavage of unusually large von Willebrand factor multimers", Blood, vol. 106, No. 13, Dec. 15, 2005, pp. 4199-4209.

Kenji Soejima, et al., "ADAMTS-13 cysteine-rich/spacer domains are functionally essential for von Willebrand factor cleavage", Blood, vol. 102, No. 9, Nov. 1, 2003, pp. 3232-3237.

Kenji Soejima, et al., "Analysis on the Molecular Species and Concentration of Circulating ADAMTS13 in Blood", The Japanese Biochemical Society, vol. 139, No. 1, 2006, pp. 147-154.

ADAMTS-13 precursor (A disintegrin and metalloproteinase with thrombospondin motifs 13) (ADAM-TS 13) (von Willebrand factor-cleaving protease) (vWF-cleaving protease) (vWF-CP), NCBI Entrez Protein, Accession No. Q76LX8, Ver. Q76LX8 GI: 74749836, Jun. 12, 2007, 20 pages. <URL:http://www.ncbi.nlm.nih.gov/sviewer/viewer.fcgi?74749836:PROT:4738637>.

Christoph Klaus, et al., "Epitope mapping of ADAMTS13 autoantibodies in acquired thrombotic thrombocytopenic purpura", Blood, vol. 103, No. 12, Jun. 15, 2004, pp. 4514-4519.

Wenhua Zhou, et al., "Enzymatically Active ADAMTS13 Variants Are Not Inhibited by Anti-ADAMTS13 Autoantibodies", The Journal of Biological Chemistry, vol. 280, No. 48, Dec. 2, 2005, pp. 39934-39941.

(Continued)

*Primary Examiner* — Tekchand Saidha
(74) *Attorney, Agent, or Firm* — Oblon, Spivak, McClelland, Maier & Neustadt, L.L.P.

(57) ABSTRACT

An enhanced disintegrin-like domain, and metalloprotease, with an isolated human thrombospondin type 1 motif, member 13 (ADAMTS-13) that includes substitutions at one or more positions in the isolated human ADAMTS-13.

9 Claims, 10 Drawing Sheets

(56) References Cited

OTHER PUBLICATIONS

Koichi Kokame et al., "von Willebrand Inshi Setsudan Koso o Cord suru Hito ADAMTS13 Idenshi no Hen'i to Tagata", Seikagaku, vol. 74, No. 8, 2002, (lecture No. 4P-460), p. 1040 (Previously filed, submitting English translation only).

Ayami Isonishi, et al., "Ko ADAMTS13 Mouse Monoclonal Kotai no Sakusei to Sono Seijo", Japanese Journal of Thrombosis and Hemostasis, vol. 15, No. 5, 2004, (lecture No. 0-07), p. 422 (Previously filed, submitting English translation only).

Extended European Search Report issued Aug. 23, 2010 in PCT/JP2008061211.

Koichi Kokame, et al., "Mutations and common polymorphisms in ADAMTS13 gene responsible for von Willebrand factor-cleaving protease activity", Proceedings of the National Academy of Sciences of the United States (PNAS), National Academy of Science, US LNKD-DOI: 10.1073/PNAS.172277399, vol. 99, No. 18, XP-002979374, Sep. 3, 2002, pp. 11902-11907.

The Extended European Search Report issued Apr. 27, 2012, in Application No. / Patent No. 11003287.7-2403 /2374878.

Lindsay M. Ricketts, et al., "O-Fucosylation is Required for ADAMTS13 Secretion", The Journal of Biological Chemistry, vol. 282, No. 23, XP-002672548, Jun. 8, 2007, pp. 17014-17023.

Office Action as received in the European Patent Application No. 11003287.7 dated May 22, 2013.

Office Action as received in the European Patent Application No. 08777372.7 dated May 24, 2013.

ADAMTS-13 MUTANT

This application is a divisional application of U.S. application Ser. No. 12/666,051, allowed, and incorporated herein by reference, which was a National Stage of PCT/JP08/061211 filed Jun. 19, 2008 and claims the benefit of JP 2007-164531 filed Jun. 22, 2007, JP 2008-020012 filed Jan. 31, 2008, and JP 2008-020177 filed Jan. 31, 2008.

TECHNICAL FIELD

The present invention relates to a mutant of ADAMTS-13 which is an enzyme capable of cleaving von Willebrand factor (hereinafter referred to as "VWF") at Tyr-Met site in A2 domain. Specifically, the present invention relates to a method of preparing ADAMTS-13 mutant having an enhanced enzymatic activity or a reduced reactivity to a neutralizing autoantibody by substituting amino acid residues specific to ADAMTS-13. In addition, the present invention relates to a mutant obtained by said method, a pharmaceutical composition comprising as an active ingredient said mutant, and a pharmaceutical preparation for treating thrombosis comprising said pharmaceutical composition.

BACKGROUND ART

ADAMTS-13 is a zinc-metalloprotease belonging to ADAMTS (a disintegrin-like domain, and metalloprotease, with thrombospondin type 1 motif) family and specifically cleaves von Willebrand factor (VWF) at Tyr1605-Met1606, which corresponds to 842-843 after cleavage of a preprosequence (VWF cleavage enzyme: VWF-Cleaving Protease, VWF-CP)(see e.g. Non-patent reference 1). ADAMTS-13 is known to be an activity modulation factor of VWF that is an important factor of platelet aggregation. VWF released through stimulation or circulating in blood is important in forming platelet thrombus because it plays a role as a collaboration with collagen on platelet adhesion and agglutination in the subendothelial tissue of a damaged vascular wall (e.g. see Non-patent reference 2).

It is considered that VWF is subjected to conformational change by intravascular shear force in blood circulation to thereby expose A2 domain, and Tyr1605-Met1606 therein, ADAMTS-13 cleavage site, is rapidly hydrolyzed by ADAMTS-13. Anderson et al. evaluated a catalytic efficiency of ADAMTS-13 using as a substrate VWF previously subjected to guanidinium hydrochloride to induce the conformational change (see e.g. Non-patent reference 3). The result showed that kcat was up to 0.83 $min^{-1}$ and kcat/Km was 55 $\mu M^{-1} min^{-1}$, which are lower than those of the other enzymes of a coagulation system to natural high molecular weight substrates, indicating that ADAMTS-13 has a lower enzymatic activity.

Thrombotic thrombocytopenic purpura (hereinafter also referred to as "TTP") caused by a reduced activity of ADAMTS-13 is classified into a congenital TTP and an acquired TTP. The congenital TTP is hereditary and caused by a molecular abnormality of ADAMTS-13 (also called Upshow Schulmann syndrome (USS)) and the acquired TTP is positive in a neutralizing autoantibody to ADAMTS-13. While a plasma transfusion is currently conducted to supplement ADAMTS-13 for treating the congenital TTP, it is desired that an ADAMTS-13 concentrate or a recombinant formulation is alternatively used for said treating in future. Moreover, a plasmapheresis is generally conducted to both remove the neutralizing antibody and to supplement ADAMTS-13 for treating the acquired TTP.

It has often reported that the molecular abnormality of ADAMTS-13 is found in patients with congenital TTP (USS) wherein a missense and/or nonsense mutation is found throughout the molecule. However, the pathogenesis of TTP starting in adult are also found, suggesting that possibly the congenital reduced ADAMTS-13 is not the only trigger of the pathogenesis of TTP. Considering that there are cases of the pathogenesis of congenital TTP during a pregnancy (VWF in blood may increase to 300% of the normal value during late pregnancy), the systemic platelet thrombus formation arising from TTP may be caused by the increased VWF in blood induced by the second trigger such as an environment factor or a genetic factor in addition to the reduced ADAMTS-13 in blood. Indeed, the present inventors have found that a re-event rate of acute myocardial infarction (hereinafter also referred to as "AMI") within 1 year is significantly high when the ratio between VWF and ADAMTS-13 in blood (VWF/ADAMTS-13) after 24 hours of the onset of AMI exceeds a certain value (see e.g. Patent reference 1).

In addition, an ADAMTS-13 antigen level in plasma of patients with thrombotic disease, including disseminated intravascular coagulation (DIC), hemolytic-uremic syndrome (HUS), deep vein thrombosis (DVT), TTP, pulmonary embolism, cerebral infarction and systemic lupus erythematosus (SLE), is significantly reduced compared to healthy adult (see e.g. Patent reference 2), wherein an ADAMTS-13 antigen level is measured with sandwich ELISA using a monoclonal antibody. Moreover, with respect to DIC associated with septicemia, it was shown that patients having ADAMTS-13 blood level of less than 20% is significantly likely to develop nephropathy as compared to patients having ADAMTS-13 blood level of 20% or more (see e.g. Non-patent reference 4).

Meanwhile, endothelial cells stimulated by inflammatory cytokine, IL-8 and/or TNF-α, induce a release of unusually large (UL) VWF that has a larger multimer structure than normal. There is also an experimental result that IL-6 inhibits a VWF cleaving activity of ADSAMTS-13 under a shear stress of blood Flow (ex vivo). Therefore, it is suggested that there is an association between inflammation and thrombus formation (see e.g. Non-patent reference 5).

In addition, it is reported that ciga toxin which causes HUS stimulates vascular endothelial cells to promote ULVWF release and inhibits the activity of ADAMTS-13. It seems possible that HUS is improved by administering ADAMTS-13 to patients with HUS (see e.g. Non-patent reference 6). Thus, when the disease as stated above may be aggravated due to an imbalance involving the reduced ADAMTS-13 and the elevated VWF, administration of ADAMTS-13 may alleviate the condition of the disease.

ADAMTS-13 as previously described belongs to a metalloprotease group called ADAMTS family. ADAMTS-1 to -20 are known as a member of this family (ADAMTS-5 is identical to ADAMTS-11). ADAMTS-13 as well as the other members of ADAMTS family has a multidomain structure (FIG. 1). The amino acid sequence of ADAMTS-13 is encoded by a DNA which contains 4284 bases and ranges from a start codon ATG(Met) to a stop codon TGA. An ADAMTS-13 gene has 29 Exons on the chromosome 9q34 and 37 kb in full-length. It is revealed via the gene sequencing of ADAMTS-13 protein that ADAMTS-13 protein has 1427 amino acid residues in the precursor thereof and 10 asparagine-linked glycosylation potential sites and is a large single-strand glycoprotein (Patent reference 4).

In a process of biosynthesis, a preprosequence of 74 residues is cleaved by a processing endoprotease Furin to provide a mature form containing 1353 amino acid residues. RQRR sequence (SEQ ID NO: 80), a cleaved motif of Furin, at the end of preprosequence is followed by a metalloprotease domain that contains a Reprolysin type zinc chelate domain comprising a consensus sequence HEXXHXXGXXHD (SEQ ID NO: 81). Then, via a disintegrin-like domain which is found in a snake venom metalloprotease, there follows the first Tsp1 motif (Tsp1-1) consisting of about 50 to 60 residues which is generally thought to be important for a molecular recognition and then a cysteine-rich domain containing one of a cell adherence motif, Arg-Gly-Asp (RGD) sequence. A spacer domain containing about 130 amino acid residues without cysteine residue then follows, and again Tsp1 motif is repeated (Tsp1-2 to Tsp1-8) followed by CUB 1 and 2 domains that have firstly been found in complement components C1r or C1s. These CUB domains are characteristic of ADAMTS-13 because among ADAMTS family only ADAMTS-13 has these domains. The present inventors have previously identified from the metalloprotease domain to spacer domain of ADAMTS-13 as domains essential for exerting an enzymatic activity or as an epitope for antibody neutralization (see e.g. Patent reference 3, and Non-patent references 7 and 8).

Patent reference 1: JP-A-2007-248395
Patent reference 2: WO2005/062054
Patent reference 3: WO2004/029242
Patent reference 4: WO2002/088366
Non-patent reference 1: Soejima, K., Mimura, N., Hirashima, M., Maeda, H., Hamamoto, T., Nakagaki, T. & Nozaki, C.: A novel human metalloprotease synthesized in the liver and secreted into the blood: possibly, the von Willebrand factor-cleaving protease? J. Biochem., 130: p. 475-480, 2001
Non-patent reference 2: Soejima, K. & Nakagaki, T.: Interplay between ADAMTS13 and von Willebrand factor in inherited and acquired thrombotic microangiopathies. Semin. Hematol., 42: p. 56-62, 2005
Non-patent reference 3: Anderson, P. J., Kokame, K. & Sadler, J. E.: Zinc and calcium ions cooperatively modulate ADAMTS13 activity. J. Biol. Chem., 281: p. 850-857, 2006
Non-patent reference 4: Ono, T., Mimuro, J., Madoiwa, S., Soejima, K., Kashiwakura, Y., Ishiwata, A., Takano, K., Ohmori, T. & Sakata, Y.: Severe secondary deficiency of von Willebrand factor-cleaving protease (ADAMTS13) in patients with sepsis-induced disseminated intravascular coagulation: its correlation with development of renal failure. Blood, 107: p. 528-534, 2006
Non-patent reference 5: Bernardo, A., Ball, C., Nolasco, L., Moake, J. F. & Dong, J. F.: Effects of inflammatory cytokines on the release and cleavage of the endothelial cell-derived ultralarge von Willebrand factor multimers under flow. Blood, 104: p. 100-106, 2004
Non-patent reference 6: Nolasco, L. H., Turner, N. A., Bernardo, A., Tao, Z., Cleary, T. G., Dong, J. F. & Moake, J. L.: Hemolytic uremic syndrome-associated Shiga toxins promote endothelial-cell secretion and impair ADAMTS13 cleavage of unusually large von Willebrand factor multimers. Blood, 106: p. 4199-4209, 2005
Non-patent reference 7: Soejima, K., Matsumoto, M., Kokame, K., Yagi, H., Ishizashi, H., Maeda, H., Nozaki, C., Miyata, T., Fujimura, Y. & Nakagaki, T.: ADAMTS-13 cysteine-rich/spacer domains are functionally essential for von Willebrand factor cleavage. Blood, 102: p. 3232-3237, 2003
Non-patent reference 8: Soejima, K., Nakamura, H., Hirashima, M., Morikawa, W., Nozaki, C. & Nakagaki, T.: Analysis on the molecular species and concentration of circulating ADAMTS13 in blood. J. Biochem., 139: p. 147-154, 2006

DISCLOSURE OF THE INVENTION

Technical Problem to be Solved by the Invention

Thus, the present invention enables the broad application as described above by preparing ADAMTS-13 mutant having a higher activity. Moreover, the mutant which has a reduced reactivity to a neutralizing antibody while holding the enzymatic activity may be applied to the acquired TTP. ADAMTS-13 mutant having such properties has never been reported so far.

Therefore, the technical problem to be solved by the present invention is to provide ADAMTS-13 mutant having an efficiently high activity for treating TTP etc. or a reduced reactivity to a neutralizing antibody.

Means for Solving the Problems

Under these circumstances, the present inventors have earnestly studied to develop ADAMTS-13 mutant having a high enzymatic activity or the mutant maintaining the enzymatic activity while the reactivity thereof with a neutralizing antibody is reduced by altering an epitope for a neutralizing antibody to thereby complete the present invention. The present inventors have succeeded in preparing ADAMTS-13W688X protein mutant which has an enhanced enzymatic activity or a reduced reactivity with a neutralizing antibody (hereinafter also referred to as "ADAMTS-13 mutant") by substitution of an amino acid contained in the disintegrin-like domain, the cysteine-rich domain or the spacer domain of a C-terminal deletion mutant W688X. Said C-terminal deletion mutant W688X (hereinafter also referred to as "ADAMTS-13W688X protein"; see Patent reference 3 and Non-patent reference 7) is a minimum unit of ADAMTS-13 exerting the activity and is provided by deleting amino acid residues ranging from the 689th amino acid to the C terminus from the 1427 amino acid residues. That is, the present invention is as described below. In addition, the modification according to the present invention may also be accomplished using a full-length of ADAMTS-13 (wild type strain) molecule.

(1) ADAMTS-13 mutant wherein at least one charged amino acid in a disintegrin-like domain, a cysteine-rich domain or a spacer domain of ADAMTS-13 other than the following amino acids is substituted with a different amino acid: arginine at position 326, aspartic acid at position 330, aspartic acid at position 343 and arginine at position 349 in the disintegrin-like domain, aspartic acid at position 480, arginine at position 488, arginine at position 498, arginine at position 507, aspartic acid at position 533 and aspartic acid at position 543 in the cysteine-rich domain, and glutamic acid at position 641 and arginine at position 660 in the spacer domain.

(2) The mutant according to (1) wherein said different amino acid is an uncharged amino acid.

(3) The mutant according to (1) or (2) wherein the charged amino acid to be substituted is an amino acid present in or around the neutralizing antibody recognition epitope including at least one of arginine at position 312, lysine at position 318, arginine at position 568, glutamic acid at position 569, arginine at position 589, lysine at position 608, glutamic acid at position 634 or aspartic acid at position 635.

(4) The mutant according to (1) or (2) wherein the charged amino acid to be substituted is selected from the group consisting of aspartic acid at position 298, arginine at position 312, arginine at position 326, glutamic acid at position 327, arginine at position 370, arginine at position 452, aspartic acid at position 504, arginine at position 514, aspartic acid at position 537, arginine at position 568 and arginine at position 659.

(5) The mutant according to any one of (2)-(4) wherein the uncharged amino acid is selected from the group consisting of alanine, glycine, proline, serine and threonine.

(6) A method of enhancing an enzymatic activity of ADAMTS-13 wherein at least one charged amino acid in a disintegrin-like domain, a cysteine-rich domain or a spacer domain of ADAMTS-13 other than the following amino acids is substituted with a different amino acid: arginine at position 326, aspartic acid at position 330, aspartic acid at position 343 and arginine at position 349 in the disintegrin-like domain, aspartic acid at position 480, arginine at position 488, arginine at position 498, arginine at position 507, aspartic acid at position 533 and aspartic acid at position 543 in the cysteine-rich domain, and glutamic acid at position 641 and arginine at position 660 in the spacer domain.

(7) A method of reducing a reactivity of ADAMTS-13 to an anti-ADAMTS-13 neutralizing antibody, wherein at least one charged amino acid in a disintegrin-like domain, a cysteine-rich domain or a spacer domain of ADAMTS-13 other than the following amino acids is substituted with a different amino acid: arginine at position 326, aspartic acid at position 330, aspartic acid at position 343 and arginine at position 349 in the disintegrin-like domain, aspartic acid at position 480, arginine at position 488, arginine at position 498, arginine at position 507, aspartic acid at position 533 and aspartic acid at position 543 in the cysteine-rich domain, and glutamic acid at position 641 and arginine at position 660 in the spacer domain.

(8) The method according to (6) or (7) wherein the different amino acid is an uncharged amino acid.

(9) The method according to any one of (6)-(8) wherein the charged amino acid to be substituted is present in or around the neutralizing antibody recognition epitope, including at least one of arginine at position 312, lysine at position 318, arginine at position 568, glutamic acid at position 569, arginine at position 589, lysine at position 608, glutamic acid at position 634, aspartic acid at position 635 or arginine at position 639.

(10) The method according to any one of (6)-(8) wherein the charged amino acid to be substituted is selected from the group consisting of aspartic acid at position 298, arginine at position 312, arginine at position 326, glutamic acid at position 327, arginine at position 370, arginine at position 452, aspartic acid at position 504, arginine at position 514, aspartic acid at position 537, arginine at position 568 and arginine at position 659.

(11) The method according to any one of (8)-(10) wherein the uncharged amino acid is selected from the group consisting of alanine, glycine, proline, serine and threonine.

(12) A pharmaceutical composition containing as an active ingredient the ADAMTS-13 mutant of any one of (1)-(5).

(13) A therapeutic agent for thrombotic disease comprising as an active ingredient the ADAMTS-13 mutant of any one of (1)-(5).

(14) The therapeutic agent according to (13) wherein the thrombotic disease is disseminated intravascular coagulation (DIC), hemolytic-uremic syndrome (HUS), deep vein thrombosis (DVT), thrombotic thrombocytopenic purpura (TTP), myocardial infarction, pulmonary embolism, cerebral infarction or systemic lupus erythematosus (SLE).

Effects of the Invention

The present invention provides a method of preparing ADAMTS-13 mutant having a high enzymatic activity and the ADAMTS-13 mutant obtained by said method. For example, ADAMTS-13 mutant is provided by substituting at least one of charged amino acids present in the disintegrin-like domain, the cysteine-rich domain or the spacer domain with an uncharged amino acid. Moreover, ADAMTS-13 mutant having a reduced reactivity to a neutralizing antibody in addition to the high enzymatic activity is provided by substituting a charged amino acid present in or around the epitope for an anti-ADAMTS-13 neutralizing antibody with an uncharged amino acid. Therefore, ADAMTS-13 mutant of the present invention may be a useful active ingredient for treating patients with thrombosis and expected to provide a good effect with a small dosage. The term of "uncharged amino acid" as used herein refers to all of the amino acids other than charged amino acids (lysine, arginine, glutamic acid and aspartic acid).

BRIEF DESCRIPTION OF DRAWINGS

FIG. 1 shows a gene structure and a protein domain structure of ADAMTS-13. Black dots indicate 10 N-linked glycosylation potential sites. FIG. 1 discloses "RQRR" as SEQ ID NO: 80.

FIG. 2 shows the results of Western blot for culture supernatant of ADAMTS-13 mutant.

FIG. 3 shows evaluation of a cleaving activity of ADAMTS-13 mutant to a synthetic substrate FRETS-VWF73. The specific activity (U=units/μg) is shown as a hydrolytic activity of the mutant (units) per the amount of protein of the mutant (the amount of antigen) (μg). The relative activity (Umutant/Uwt) was obtained from a ratio of the specific activity of the mutant to that of the wild type strain (U=U(mutant)/U(wild type strain)). The specific activity (U=units/μg); U=the hydrolytic activity of the mutant (units)/the amount of protein of the mutant (the amount of antigen) (μg). The relative activity (Umutant/Uwt); U mutant/U wild type strain.

FIG. 4 shows evaluation of a cleaving activity of ADAMTS-13 mutant to a natural substrate VWF. The specific activity (U=units/μg) is shown as the hydrolytic activity of the mutant (units) per the amount of protein of the mutant (the amount of antigen) (μg). The relative activity (Umutant/Uwt) was obtained from a ratio of the specific activity of the mutant to that of the wild type strain (U=U mutant/U wild type strain). The specific activity (U=units/μg); U=the hydrolytic activity of the mutant (units)/the amount of protein of the mutant (the amount of antigen) (μg). The relative activity (Umutant/Uwt); U mutant/U wild type strain.

FIG. 5 shows evaluation of a binding ability of ADAMTS-13 mutant to VWF immobilized on ELISA plate. The specific activity (U=units/μg) is shown as the binding activity of the mutant (units) per the amount of protein of the mutant (the amount of antigen)(μg). The relative activity (Umutant/Uwt) was obtained from a ratio of the specific activity of mutant to that of the wild type strain (U=U mutant/U wild type strain). The specific activity (U=units/μg); U=the binding activity of the mutant (units)/the amount of protein of the mutant (the amount of antigen) (μg). The relative activity (Umutant/Uwt); U mutant/U wild type strain.

FIG. 6 shows the results of Western blot for an epitope analysis of a neutralizing murine monoclonal antibody. The arrows indicate the estimated epitope amino acids.

BEST MODE FOR CARRYING OUT THE INVENTION

Figure 1:
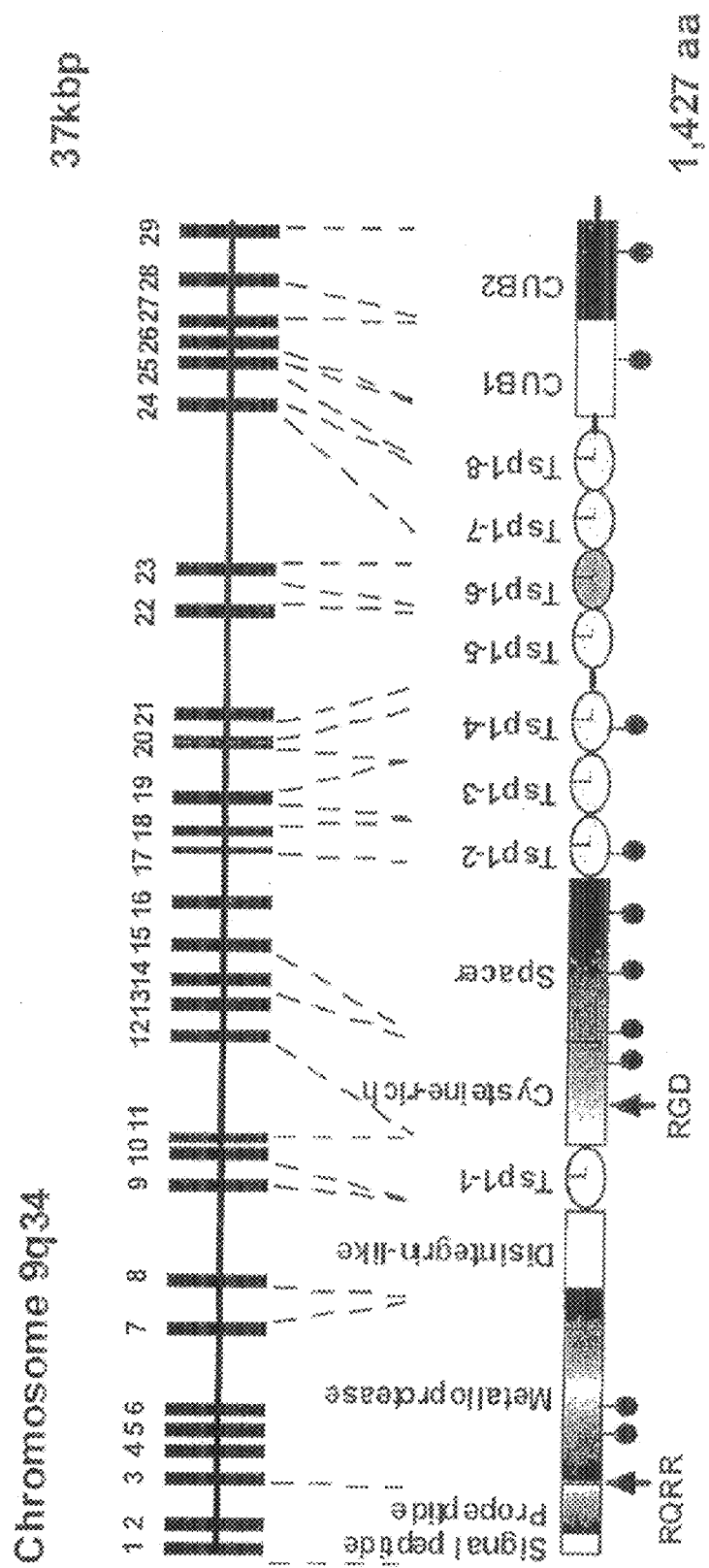

The present invention is characterized by a method of enhancing an enzymatic activity of ADAMTS-13 and/or a method of reducing the reactivity to an anti-ADAMTS-13 neutralizing antibody as well as a mutant of ADAMTS-13 prepared by said methods. The method of the present invention is accomplished by substituting a charged amino acid (arginine (R), lysine (K), glutamic acid (E), aspartic acid (D)) in the disintegrin-like domain, the cysteine-rich domain or the spacer domain with a different amino acid, especially an uncharged amino acid on the basis of the minimum unit of ADAMTS-13 exerting the activity (ADAMTS-13W688X protein), and evaluating the enzymatic activity of the resulting mutant and the reactivity thereof to a neutralizing monoclonal antibody. Detail of the method is described herein below.

The gene W688X encoding the minimum unit of ADAMTS-13 exerting the activity (hereinafter also referred to as "ADAMTS-13W688X gene") may be obtained, for example, by designing a PCR primer on the basis of the sequence as described in Non-patent reference 7 and Patent reference 3 and conducting PCR using as a template cDNA derived from human organs or cells producing ADAMTS-13. In particular, the ADAMTS-13W688X gene may be prepared as described below. First, total RNAs are extracted from human hepatocytes and then mRNAs are purified therefrom. The resulting mRNAs are converted to cDNAs, then PCR reaction is conducted using PCR primers designed depending on each of the gene sequences, and the resulting PCR products are incorporated into a plasmid vector which is introduced into *E. coli*. The clone containing cDNA encoding the desired protein is chosen among *E. coli* colonies. For the extraction of total RNAs, commercially available reagents such as TRIzol reagent (GIBCO BRL) and ISOGEN (NIPPON GENE Co., Ltd.) may be used. For the purification of mRNAs, commercially available kits such as mRNA Purification Kit (Amersham BioSciences) may be used. For the conversion to cDNAs, commercially available kits for preparing cDNA library such as SuperScript plasmid system for cDNA synthesis and plasmid cloning (GIBCO BRL) may be used. For practically obtaining the ADAMTS-13W688X gene, a commercially available cDNA library such as e.g. Human Liver Marathon-Ready cDNA (BC Bioscience) may be used. The PCR primers are readily available from companies in charge of DNA synthesis (e.g. QIAGEN). It is preferred that KOZAK sequence (Kozak M, J. Mol. Biol., 196, 947 (1987)) and an adequate sequence of a restriction enzyme cleavage site is added to the 5' side of the primer. The PCR reaction may be conducted using a commercially available Advantage HF-2 PCR Kit (BC Bioscience) in accordance with the appended protocol. The base sequence of DNA fragments obtained from PCR is determined by a DNA sequencer, e.g. CEQ2000XL DNA Analysis System (Beckman) after the cloning using a TA cloning kit (Invitrogen Corporation) etc.

In order to introduce a point mutation to the resulting ADAMTS-13W688X gene, site-directed mutagenesis may generally be used. Practically, the introduction of a point mutation to the ADAMTS-13W688X gene is conducted using a commercially available kit such as Site-Directed Mutagenesis System (Takara: Mutan-Super Express Km, Mutan-Express Km, Mutan-K and the like), QuickChange Multi Site-Directed Mutagenesis Kit, QuickChange XL Site-Directed Mutagenesis Kit (Stratagene) and GeneTailor Site-Directed Mutagenesis System (Invitrogen) applying said technique in accordance with the appended protocol. A total of 78 primers as listed in Table 1 may be used in order to substitute any of the charged amino acids, N-linked glycosylation potential sites in the disintegrin-like domain, the cysteine-rich domain, and the spacer domain of ADAMTS-13 with alanine. Multiple point mutations may be introduced by repeating site-directed mutagenesis using as a template the ADAMTS-13W688X gene where a point mutation is introduced and different primers. A DNA sequence of the ADAMTS-13W688X gene where a point mutation is introduced may be determined by the above DNA sequencer.

The ADAMTS-13W688X gene or the ADAMTS-13W688X gene with a point mutation (hereinafter also referred to as "altered ADAMTS-13W688X gene") may be incorporated into an appropriate expression vector and a host may be transformed with said expression vector to allow for expression of the minimum unit of ADAMTS-13 exerting the activity (ADAMTS-13W688X protein) and the mutant thereof (ADAMTS-13 mutant). As a host, a bacterial cell, a yeast cell, an animal cell, a plant cell and an insect cell etc. may be used as commonly used to express a foreign protein as long as efficacy as a therapeutic agent for thrombotic disease is exhibited. Preferably, a eukaryotic cell such as an animal cell may be used. When an animal cell is used as a host, an expression vector may be incorporated with a promoter and marker genes for selection and for gene amplification depending on the host animal cell as used. For example, for an expression vector constructed using an expression plasmid containing chicken β-actin promoter (pCAGG vector), HeLa cell, 293 cell, CHO cell, or BHK cell may be used.

The known method may be used to transform a host cell. For example, the use of calcium phosphate, the use of DEAE dextran, the method using liposomes of Lipofectin, protoplast polyethylene glycol fusion, electroporation, and the like may be employed and appropriately be selected depending on a host cell as used (Molecular Cloning (3rd Ed.), Vol. 3, Cold Spring Harbor Laboratory Press (2001)).

Selection and proliferation of the transformed cells may be performed by a method as usually used for transformation of animal cells. For example, the cells after transformation may be cultured using a selection medium at 37° C. for 10-14 days while appropriately exchanging the culture medium. The selection medium includes a medium generally used to cultivate animal cells such as a serum-free medium, e.g. CHO-S-SFMII medium (GIBCO-BRL), IS CHO-V medium (IS Japan Co., Ltd.), YMM medium or a serum medium, e.g. MEM α medium, RPMI medium or Dulbecco MEM medium (all from GIBCO-BRL) supplemented with about 5-10% fetal bovine serum. The selection medium may contain methotrexate, G418, and the like depending on the employed selection marker. Upon the culture, untransformed cells are not alive and only transformed cells are grown. In addition, the transformed cells are subjected to limiting dilution etc. to select and clone cell strains of interest producing the ADAMTS-13W688X protein or the ADAMTS-13 mutant.

To purify the ADAMTS-13W688X protein or the ADAMTS-13 mutant from the cells producing said protein, a purification method generally used in the protein chemistry may be used. The purification method includes, for example, centrifugation, salting-out, ultrafiltration, isoelectric precipitation, electrophoresis, ion-exchange chromatography, gel filtration, affinity chromatography, hydrophobic chromatography, hydroxyapatite chromatography and CS resin chromatography in combination thereof. An amount of the obtained protein may be determined using a reagent for protein measurement such as BCA Protein Assay Reagent Kit (Pierce Biotechnology, Inc), Protein Assay Kit (BIO-RAD, Inc), and the like.

The ADAMTS-13W688X protein or the ADAMTS-13 mutant may be expressed in the form of a fusion with other polypeptide or peptide to allow for easier purification. A vector expressing such a fusion protein includes the system which may express a fusion protein associated with FLAG tag (SIGMA), a GST fusion protein purification system which can prepare a fusion protein with glutathione S transferase (GST) (Amersham Pharmacia), an HAT protein expression/purification system (Clontech Inc.) which is capable of adding oligohistidine, Magne His Protein Purification System (Promega Inc), and the like. For example, as described in Examples of the present invention, the ADAMTS-13 mutant expression product expressed as a fusion protein with FLAG tag is specifically purified using agarose gel immobilized with an anti-FLAGM2 monoclonal antibody (SIGMA CORPORATION). The detection of the ADAMTS-13W688X protein or the ADAMTS-13 mutant may be conducted by a method on the basis of a molecular size such as SDS-PAGE, gel filtration, and the like or a method on the basis of an antigen-antibody reaction such as ELISA, Western blot, dot blot, and the like. The above methods are all commonly used to determine a foreign protein and may be selected in accordance with the purpose.

To evaluate the ability of the ADAMTS-13 mutant as an enzyme, the activity to bind to or degrade von Willebrand factor (VWF) derived from human plasma or partially synthesized peptide of VWF may be measured by a method such as ELISA and the like using an antibody to ADAMTS-13 or an antibody to FLAG and compared to the activity of a wild-type ADAMTS-13W688X protein with no amino acid substitution. ELISA may be constructed by a common procedure. VWF derived from human plasma and an antibody to ADAMTS-13 for ELISA may be obtained according to the methods of Non-patent reference 1 and Non-patent reference 8, respectively. A commercially available fluorescently-labeled FRETS-VWF73 (PEPTIDE INSTITUTE, INC.) may be used as a partially synthesized peptide of VWF. The resulting ADAMTS-13 mutant having a higher enzymatic activity than the ADAMTS-13W688X protein is substituted with charged amino acids other than the following amino acids with alanine: aspartic acid at position 343, arginine at position 349, aspartic acid at position 480, arginine at position 488, arginine at position 498, arginine at position 507, aspartic acid at position 533, aspartic acid at position 543, glutamic acid at position 641 and arginine at position 660. The number of substitution of the charged amino acids may be at least one. These ADAMTS-13 mutants may be greatly efficacious at a low dosage in human as a therapeutic agent for e.g. thrombosis. In addition, due to the low dosage, reduction in adverse side effects may be expected.

These effects become immense by the reduced reactivity to a neutralizing autoantibody found in patients with thrombosis in addition to the elevated enzymatic activity. These ADAMTS-13 mutants may be obtained by studying an extent of binding of the ADAMTS-13 mutant having a high enzymatic activity to a neutralizing antibody using ELISA or Western Blotting (hereinafter also referred to as "WB"). The neutralizing antibody as used herein may be a polyclonal antibody or a monoclonal antibody. To obtain the monoclonal antibody, antibody producing cells such as splenocytes or lymphocytes may be collected from an animal immunized with mature dendritic cells from immature dendritic cells, the resulting cells may be fused with myeloma cell line according to Milstein et al., Method Enzymol., 73, 3-46, 1981, to prepare hybridomas which produce an antibody to a specific antigen. Alternatively, an antibody preparation technique using a phage display (Phage Display of Peptides and Proteins: A Laboratory Manual Edited by Brian K. Kay et al., Antibody Engineering: A PRACTICAL APPROACH Edited by J. McCAFFERTY et al., ANTIBODY ENGINEERING second edition edited by Carl A. K. BORREBAECK) may be used to prepare an antibody which binds to a specific antigen. For the above ELISA or WB, the resulting antibody may be labeled by fluorescence labeling, RI, biotinylation, and the like. These are all commercially available as a kit.

The resulting ADAMTS-13 mutant is preferably such that the charged amino acids comprising at least one of arginine at position 312, lysine at position 318, arginine at position 568, glutamic acid at position 569, arginine at position 589, lysine at position 608, glutamic acid at position 634, aspartic acid at position 635 or arginine at position 639 in or around the neutralizing antibody recognition epitope are substituted with alanine. Alternatively, the ADAMTS-13 mutant is preferably such that the charged amino acids selected from the group consisting of aspartic acid at position 298, arginine at position 312, arginine at position 326, glutamic acid at position 327, arginine at position 370, arginine at position 452, aspartic acid at position 504, arginine at position 514, aspartic acid at position 537, arginine at position 568 and arginine at position 659 are substituted. As described above, the number of substitution of the charged amino acids may be 1 or more.

Moreover, the charged amino acids may be substituted with not only alanine as in Examples but also with other uncharged amino acids, preferably glycine, proline, serine and threonine which are subject to easy amino acid substitution during the course of evolution (i.e. analogous amino acids)(BIOINFORMATICS A Practical Guide to the Analysis of Genes and Proteins Edited by ANDREAS D. BAXEVANIS, B. F. FRANCIS OUELLETTE, John Wiley & Sons, Inc.).

The ADAMTS-13 mutant of the present invention may be formulated into a pharmaceutical preparation for treatment, diagnosis or other uses. For example, to prepare a preparation for intravenous administration, a composition may generally be dissolved in an aqueous solution that contains physiologically compatible materials such as sodium chloride, glycine etc. and has a physiologically compatible, buffered pH. A lyophilized formulation may be employed as a final form to enable prolonged stability. A guideline for a composition for intravenous administration is established by the Government's regulation, e.g. "Minimum Requirements for Biological Products". A pharmaceutical composition of the present invention comprising as an active ingredient the ADAMTS-13 mutant may specifically be used in patients having a reduced ADAMTS-13 level such as patients with disseminated intravascular coagulation (DIC), hemolytic-uremic syndrome (HUS), deep vein thrombosis (DVT), thrombotic thrombocytopenic purpura (TTP), myocardial infarction, pulmonary embolism, cerebral infarction, systemic lupus erythematosus (SLE), and the like. Alternatively said pharmaceutical composition may be used as a supplemental treatment in patients with an elevated blood concentration of VWF, a substrate of this enzyme, or in patients foreseen to develop ULVWF due to inflammation etc.

The present invention is explained by the following Examples which are not construed to limit the present invention. The present invention is specifically exemplified by Examples together with the appended drawings. In Examples, the mutants were expressed in culture supernatant of animal cells (HeLa). Unless otherwise instructed, reagents and devices etc. used for genetic recombination were available from TaKaRa SHUZO, Toyobo, Bio-Rad, PerkinElmer Applied, Beckman and New England Biolabs.

Example 1

Preparation of Alanine Substituents

A DNA comprising the coding region in pCR vector of the gene W688X encoding the minimum unit exerting the ADAMTS-13 activity (ADAMTS-13W688X gene) as described in Patent reference 3 with introduction of FLAG tag sequence at the C-terminal was digested with restriction enzymes XhoI/SalI and extracted. The resulting product was recloned into pKF vector attached to Site-Directed Mutagenesis kit Mutan-Super Express Km (TaKaRa). According to the package insert of the kit, the 5' phosphorylated synthetic DNA primer sequences listed in tables 1 to 4 were prepared. With these, a total of 78 plasmids were prepared containing the altered ADAMTS-13W688X genes encoding the protein wherein the desired charged amino acids were substituted with alanine. All of the altered ADAMTS-13W688X genes were confirmed by the automatic sequencer CEQ2000XL DNA Analysis System (Beckman). Table 1 shows primers for preparing mutants with substitution in the disintegrin-like domain, Table 2 for primers for preparing mutants with substitution in the cysteine-rich domain, Table 3 for primers for preparing mutants with substitution in the spacer domain, and Table 4 for primers for preparing deglycosylation mutants with substitution in the cysteine-rich and spacer domains. In the primers indicated in the Tables, the numerals on the left are a serial number of the primers and "R287A", for example, following the period indicates that the amino acid residue arginine (R) at position 287 is substituted with alanine (A). In addition, the mutation site is indicated with lower case in the base sequence.

TABLE 1

SEQ ID NOS: 2-21, left count to right column, respectively, in order of appearance.

| Primer | Base Sequence | Primer | Base Sequence |
|---|---|---|---|
| 1. R287A | GACCCGCCGgcGCCTCAACCC | 11. R349A | AGCTGCAGCgcCCTCCTCGTTC |
| 2. D298A | CACCCGCCGGcTGCGCAGCC | 12. D356A | CCTCTCCTGGcTGGGACAGAATG |
| 3. E309A | AGCGCCAACGcGCAGTGCCGC | 13. E359A | GATGGGACAGcATGTGGCGTG |
| 4. R312A | GAGCAGTGCGcCGTGGCCTTC | 14. E363A | TGTGGCGTGGcGAAGTGGTGC |
| 5. K318A | TTCGGCCCCGcGGCTGTCGCC | 15. K364A | GGCGTGGAGGcGTGGTGCTCC |
| 6. R326A | ACCTTCGCCGcGGAGCACCTG | 16. K368A | TGGTGCTCCGcGGGTCGCTGC |
| 7. E327A | TTCGCCAGGGcGCACCTGG | 17. R370A | TCCAAGGGTgcCTGCCGCTCC |
| 8. D330A | GAGCACCTGGcTATGTGCCAG | 18. R372A | GGTCGCTGCgcCTCCCTGGTG |
| 9. D340A | TGCCACACAGcCCCGCTGGAC | 19. E376A | TCCCTGGTGGcGCTGACCCCC |
| 10. D343A | GACCCGCTGGcCCAAAGCAGC | 20. R386A | GTGCATGGGgcCTGGTCTAGC |

TABLE 2

SEQ ID NOS: 22-48, left column to right column, respectively, in order of appearance.

| Primer | Base Sequence | Primer | Base Sequence |
|---|---|---|---|
| 21. R452A | CAGTGCGCCgcGACCGACGGC | 35. D516A | CCCCGGGAGGcCGGGACCCTG |
| 22. D454A | GCCAGGACCGcCGGCCAGCCG | 36. R528A | GGCAGCTGCgcGACATTTGGC |
| 23. R459A | CAGCCGCTGgcCTCCTCCCCTG | 37. D533A | TTTGGCTGTGcTGGTAGGATG |
| 24. D480A | AGCCAAGGGGcTGCTCTGTGC | 38. R535A | TGTGATGGTgcGATGGACTCC |
| 25. R484A | GCTCTGTGCgcACACATGTGC | 39. D537A | GGTAGGATGGcCTCCCAGCAG |
| 26. R488A | CACATGTGCgcGGCCATTGGC | 40. D543A | CAGGTATGGGcCAGGTGCCAG |

TABLE 2-continued

SEQ ID NOS: 22-48, left column to right column, respectively, in order of appearance.

| Primer | Base Sequence | Primer | Base Sequence |
|---|---|---|---|
| 27. E492A | GCCATTGGCGcGAGCTTCATC | 41. R544A | GTATGGGACgcGTGCCAGGTG |
| 28. K497A | TTCATCATGgcGCGTGGAGAC | 42. D551A | TGTGGTGGGGcCAACAGCACG |
| 29. R498A | ATCATGAAGgcTGGAGACAGC | 43. R558A | TGCAGCCCAgcGAAGGGCTC |
| 30. D500A | AAGCGTGGAGcCAGCTTCCTC | 44. K559A | AGCCCACGGcGGGCTCTTTC |
| 31. D504A | AGCTTCCTCGcTGGGACCCGG | 45. R566A | ACAGCTGGCgcAGCGAGAG |
| 32. R507A | GATGGGACCgcGTGTATGCC | 46. R568A | GGCAGAGCGgcAGAATATGTC |
| 33. R514A | AGTGGCCCCgcGGAGGACGGG | 47. E569A | AGAGCGAGAGcATATGTCACG |
| 34. E515A | GGCCCCCGGGcGGACGGGACC | | |

TABLE 3

SEQ ID NOS: 49-75, left column to right column, respectively, in order of appearance.

| Primer | Base Sequence | Primer | Base Sequence |
|---|---|---|---|
| 48. R589A | GCCAACCACgcGCCTCTCTTC | 62. E642A | CGCCTGGAGGcGATCCGCAC |
| 49. R598A | TTGGCGGTGgcGATCGGAGG | 63. R644A | GAGGAGATCgcCATCTGGGG |
| 50. R602A | ATCGGAGGGgcCTATGTCGTG | 64. E651A | CCCCTCCAGGcAGATGCTGAC |
| 51. K608A | GTGGCTGGGgcGATGAGCATC | 65. D652A | CTCCAGGAAGcTGCTGACATC |
| 52. E622A | TCCCTCCTGGcGGATGGTCG | 66. D654A | GAAGATGCTGcCATCCAGG |
| 53. D623A | CTCCTGGAGGcTGGTCGTGTC | 67. R659A | CAGGTTTACgcGCGGTATGG |
| 54. R625A | GAGGATGGTgcTGTCGAGTAC | 68. R660A | GTTTACAGGgcGTATGGCGAG |
| 55. E627A | GGTCGTGTCGcGTACAGAGTG | 69. E663A | CGGTATGGCGcGGAGTATGG |
| 56. R629A | GTCGAGTACgcAGTGGCCCTC | 70. E664A | TATGGCGAGGcGTATGGCAAC |
| 57. E634A | GCCCTCACCGcGGACCGGCTG | 71. R670A | AACCTCACCgcCCCAGACATC |
| 58. D635A | CTCACCGAGGcCCGGCTGCC | 72. D672A | ACCCGCCCAGcCATCACCTTC |
| 59. R636A | ACCGAGGACgcGCTGCCCCG | 73. K681A | TTCCAGCCTgcGCCACGGCAG |
| 60. R639A | CGGCTGCCCgcCCTGGAGGAG | 74. R683A | CCTAAGCCAgcGCAGGCCTG |
| 61. E641A | CCCCGCCTGGcGGAGATCCG | | |

TABLE 4

SEQ ID NOS: 76-79, respectively, in order of appearance.

| Primer | Base sequence |
|---|---|
| 75. N552A | GGTGGGGACgcCAGCACGTGC |
| 76. N579A | GTTACCCCCgcCCTGACCAG |
| 77. N614A | ATCTCCCTGCCACCACCTAC |
| 78. N667A | GAGTATGGCGCCCTCACCCGC |

Example 2

Preparation of Vector for Mutant Expression

The expression vector pCAGG (JP Patent 2824434) was digested with SalI and ligated with the plasmid containing the altered ADAMTS-13W688X genes prepared in Example 1 previously cleaved with SalI/XhoI, followed by transformation of E. coli JM109 therewith and incubation on the LB agar medium containing ampicillin to select transformed E. coli cells. The resulting colonies were incubated with a commercially available culture medium overnight, and then extraction and purification were conducted to prepare the desired expression plasmids.

Example 3

Expression in Culture Supernatant and Purification of Mutants

Figure 2:
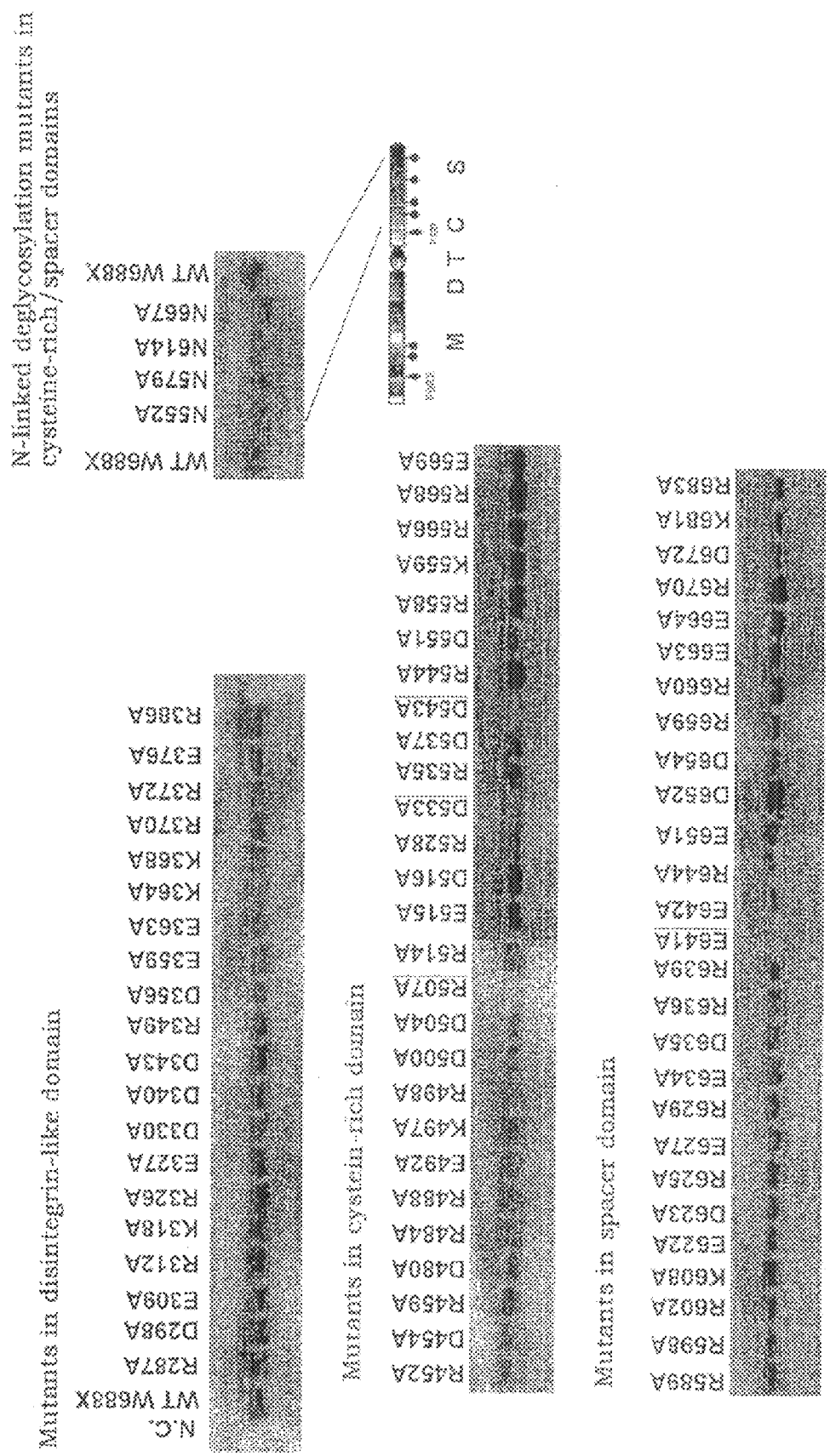

The expression vectors containing the altered ADAMTS-13W688X genes of Example 2 were transfected into HeLa cells using a commercially available Lipofectin reagent. The culture supernatant of temporary expression (15 mL) was collected on Day 3 after the gene transfection. First, Western Blotting was conducted to check whether or not the secretion was present in the culture supernatant by a common procedure using a commercially available antibody to FLAG tag (anti-FLAGM2 monoclonal antibody (SIGMA CORPORATION)). As a result, as showed in FIG. 2, for four alanine substituents: R507A(32), D533A(37) and D543A(40) in the cysteine-rich domain and E641A(61) in the spacer domain, no normal expression in culture supernatant could be found (the numeral in parenthesis of the mutants indicates the primer number; hereinafter the same). The culture supernatants other than these were concentrated to 1 mL using Centriprep YM-10 (Millipore). Due to the FLAG tag sequence possessed by all the mutants at their C-terminal, affinity purification was conducted using agarose gel with an anti-FLAGM2 monoclonal antibody immobilized thereon (SIGMA CORPORATION). The elution was conducted using a FLAG peptide solution at a concentration of 100 µg/mL in accordance with an attached protocol.

Example 4

Measurement of Hydrolytic Activity of Mutants to VWF Partial Peptide Substrate (FRETS-VWF73)

The activity of each of the mutants of Example 3 was measured using the commercially available fluorescent substrate FRETS-VWF73 (PEPTIDE INSTITUTE, INC.). A concentration of the purified protein was normalized by sandwich ELISA using the anti-human ADAMTS-13 rabbit polyclonal antibody described in Non-patent reference 8 and an HRP labeled form of the anti-FLAGM2 murine monoclonal antibody (SIGMA CORPORATION). With this, the fluorescent substrate cleaving activity was measured to quantify the specific activity. Finally, the mutants were evaluated for a relative activity as compared to the specific activity of the wild type W688X with no alanine substitution, the specific activity of which is 1. Thus, it may be concluded that when the relative activity is significantly higher than 1, the mutant will have a higher enzymatic activity than the wild type strain, and when the relative activity is significantly lower than 1, the mutant will have a lower enzymatic activity (or said amino acid is important for exerting the activity).

Figure 3:
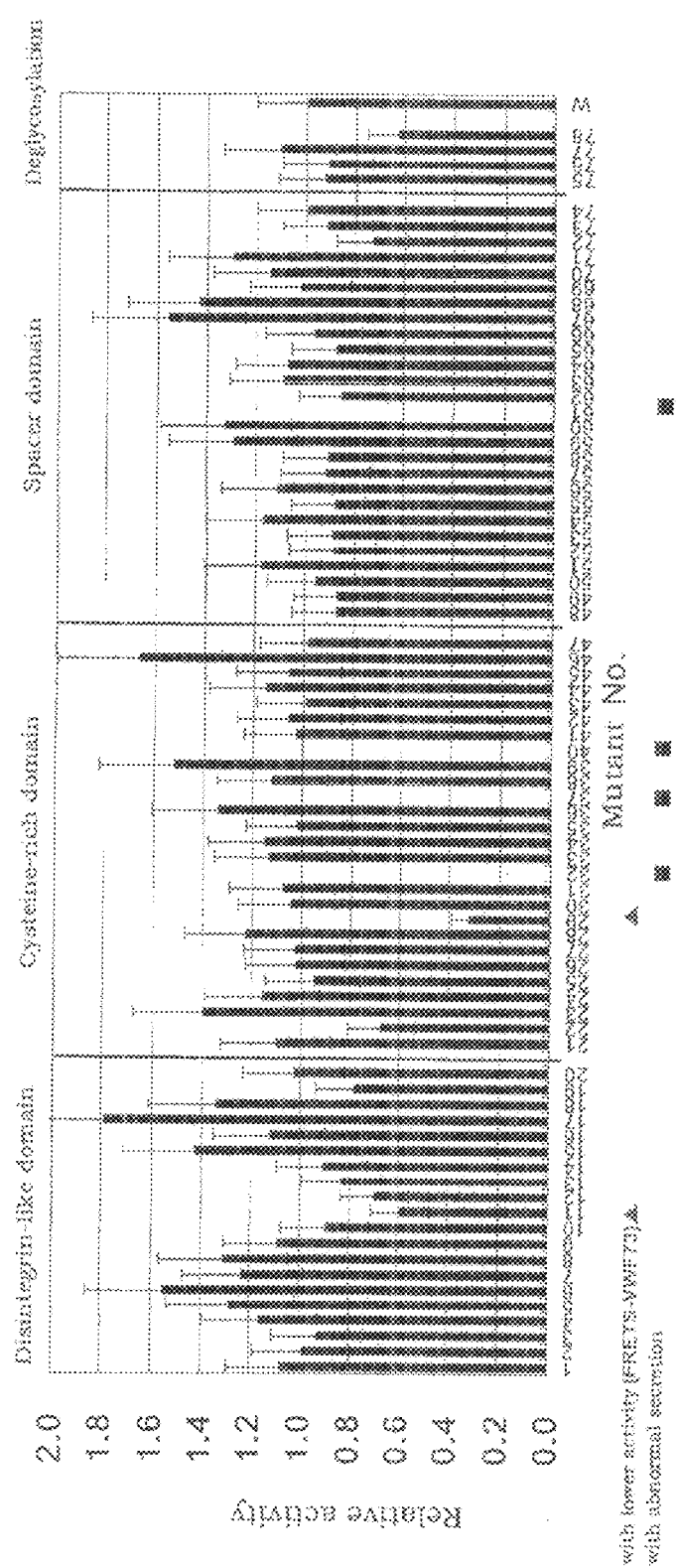

As a result, as showed in FIG. 3, the amino acid substitutions at position R349 in the disintegrin-like domain and at position R498(29) in the cysteine-rich domain led to the significantly reduced enzymatic activity (the bar graph in FIG. 3 is accompanied by the estimated experimental error of ±20% of this experimental system). On the other hand, the elevated enzymatic activity was observed for the amino acid substitutions at position R326(6), at position R370(17), at position R568(46) and at position R659(67).

Example 5

Measurement of VWF Degrading Activity of Mutants

The activity of each of the mutants of Example 3 was measured as described below using as a substrate the VWF derived from human plasma purified as described in Non-patent reference 1. Referring to Non-patent reference 3, VWF was denatured by incubation with 1.2 M guanidine hydrochloride at 37° C. for 1 h. Then, the VWF was reacted with an appropriate concentration of the ADAMTS-13 mutant at 37° C. for 1 h and the reaction was quenched with EDTA of a final concentration of 5 mM. Thereafter, a degree of cleavage of VWF was measured by collagen binding ELISA (Gerritsen, H E., Turecek, P L., Schwarz, H P., Lammle, B. & Furlan, M.: Assay of von Willebrand factor (vWF)-cleaving protease based on decreased collagen binding affinity of degraded vWF: a tool for the diagnosis of thrombotic thrombocytopenic purpura (TTP). Thromb. Haemost. 82: 1386-1389, 1999). A concentration of the purified protein was normalized by sandwich ELISA using an anti-human ADAMTS-13 rabbit polyclonal antibody described in Non-patent reference 8 and an HRP labeled form of an anti-FLAGM2 murine monoclonal antibody (SIGMA CORPORATION). With these, the fluorescent substrate cleaving activity was measured to quantify the specific activity. Finally, the mutants were evaluated for a relative activity as compared to the specific activity of wild type W688X with no alanine substitution, the specific activity of which is 1. Thus, it may be concluded that when the relative activity is significantly higher than 1, the mutant will have a higher enzymatic activity than the wild type strain, and when the relative activity is significantly lower than 1, the mutant will have a lower enzymatic activity (or said amino acid is important to exerting the activity).

Figure 4:
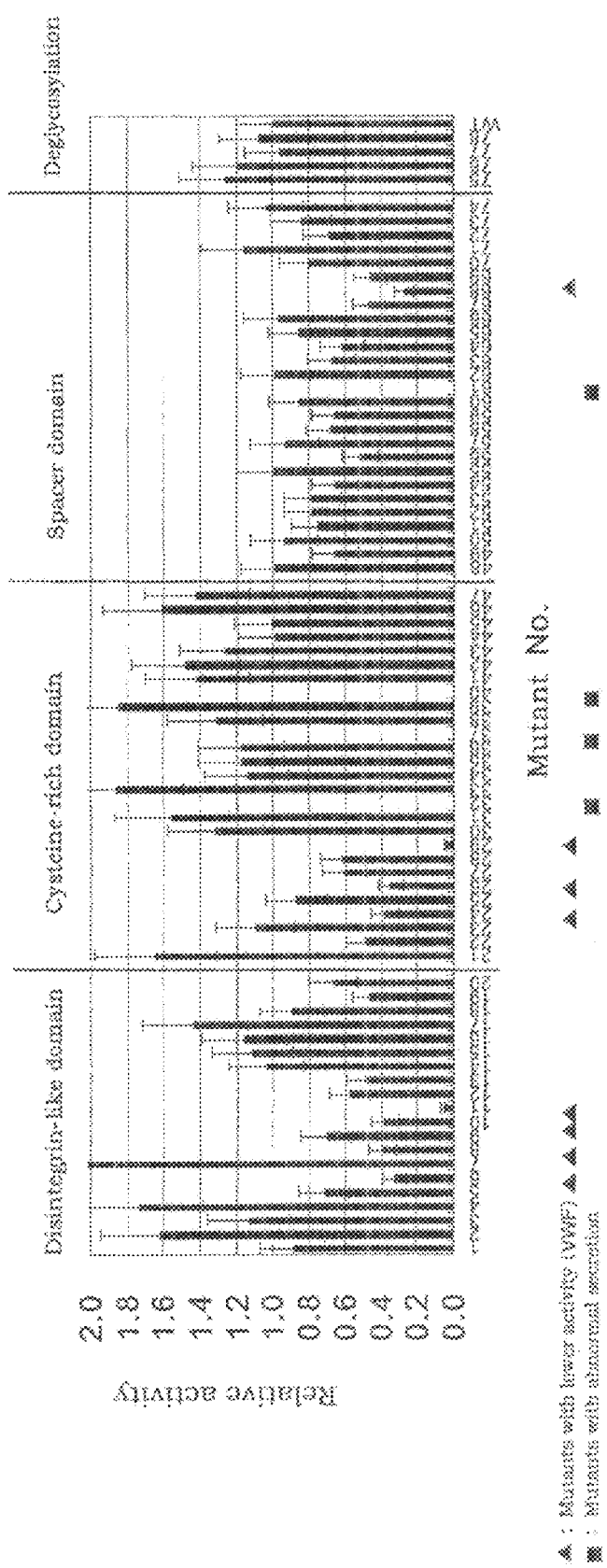

As a result, as showed in FIG. 4, the substitutions at position R326(6), at position D330(8), at position D343(10) and at position R349(11) in the disintegrin-like domain, at position D480(24), at position R488(26) and at position R498(29) in the cysteine-rich domain, and in the vicinity of position R660(68) in the spacer domain led to the reduced binding ability to VWF. On the other hand, the substitutions at position D298(2) and at position E327(7) in the disintegrin-like domain, at position R452(21), at position D504(31), at position R514(33) and at position D537(39) in the cysteine-rich domain led to the enhanced VWF cleaving activity (the bar graph in FIG. 4 is accompanied by the estimated experimental error of ±20% of this experimental system).

Example 6

Evaluation of Mutants for their Binding Ability to VWF

Each of the purified mutants of Example 3 was evaluated for their binding ability to VWF derived from human plasma immobilized on ELISA plate as described in Non-patent reference 8. The concentration was normalized by sandwich ELISA using the anti-human ADAMTS-13 rabbit polyclonal antibody and an HRP labeled form of the anti-FLAGM2 murine monoclonal antibody (SIGMA CORPORATION) as described above and the VWF binding ability per unit concentration was quantified. Finally, the mutants were evaluated for a relative activity as compared to the specific activity of wild type W688X with no alanine substitution, the specific activity of which is 1. Thus, it may be concluded that when the relative activity is significantly higher than 1, the mutant will have a higher affinity than the wild type strain, and when the relative activity is significantly lower than 1, the mutant will have a lower affinity (or said amino acid is important for the recognition of VWF).

Figure 5:
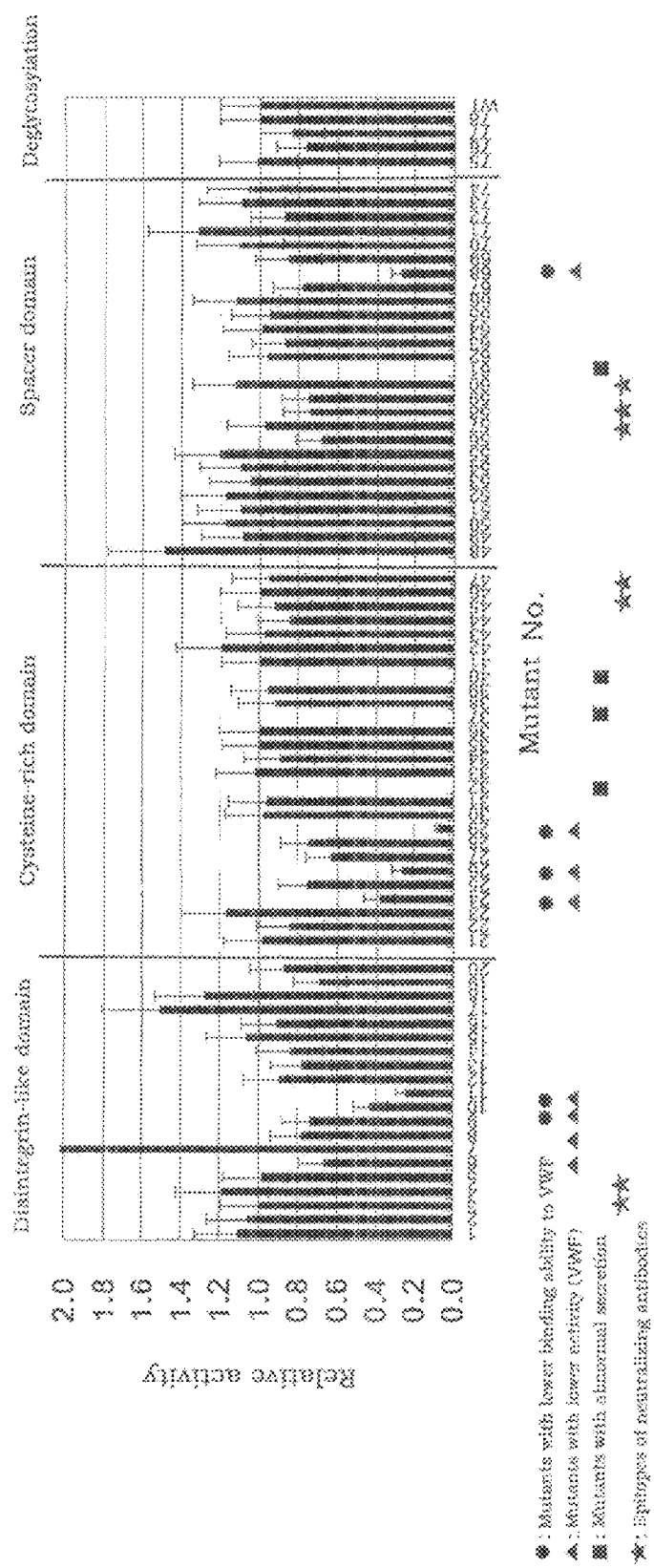

As a result, as showed in FIG. 5, the substitutions at position D343(10) and at position R349(11) in the disintegrin-like domain, at position D480(24), at position R488(26) and at position R498(29) in the cysteine-rich domain and at position R660(68) in the spacer domain led to the reduced binding ability to VWF. On the other hand, the substitutions at position E327(7) in the disintegrin-like domain led to the enhanced affinity to VWF (the bar graph in FIG. 5 is accompanied by the estimated experimental error of ±20% of this experimental system).

Example 7

Epitope Analysis of Neutralizing Antibody 1

Figure 6:
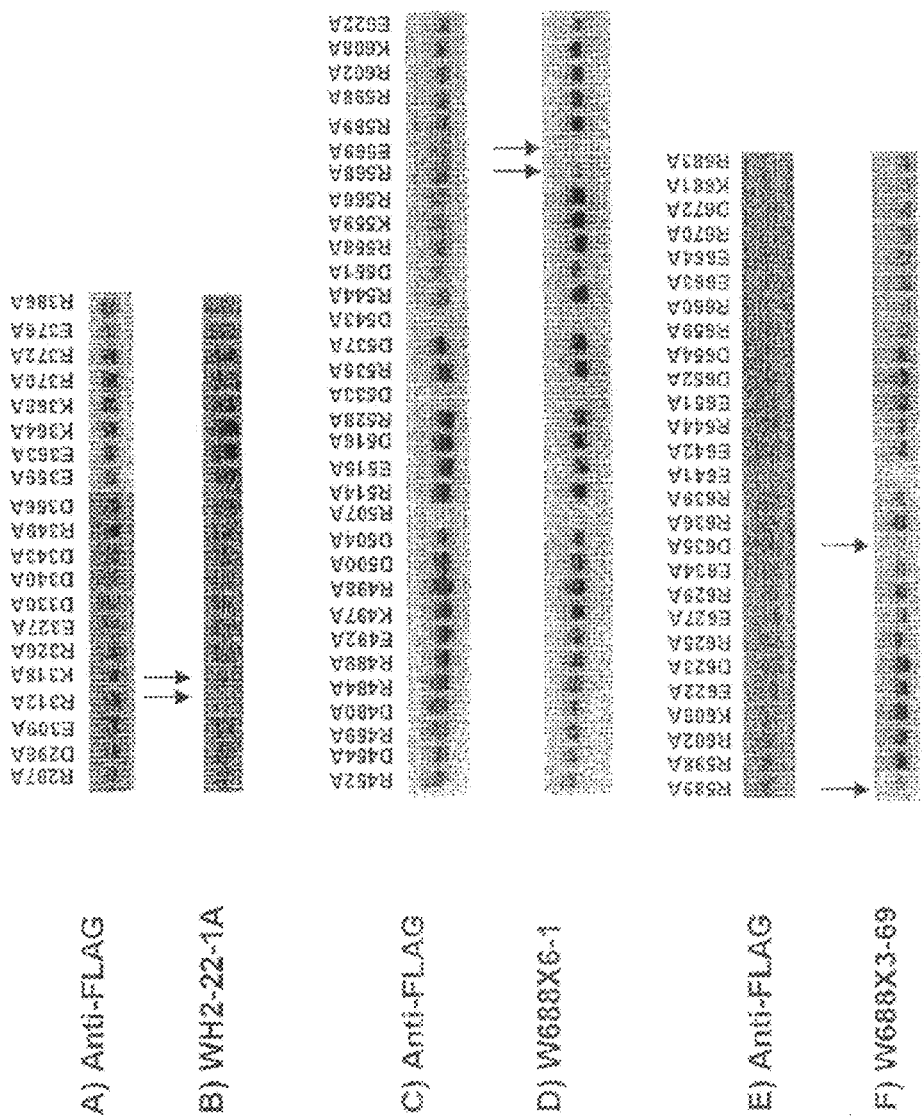

Following the Western Blotting (WB) in Example 3 to confirm the expression, the anti-FLAG antibody was released by a WB separating solution (NAKARAI), reacted again with the murine monoclonal antibodies (WH2-22-1A, W688X6-1 and W688X3-69) having an ability to neutralize the ADAMTS-13 activity established by the present inventor using common procedures as described in Non-patent reference 8, and visualized with an HRP labeled form of the anti-murine immunoglobulin (VECTOR) wherein the epitopes of the antibodies were confirmed by a reduced color intensity (FIG. 6). As a result, it was revealed that the vicinity of R312 and K318 for WH2-22-1A, the vicinity of R568 and E569 for W688X6-1 and the vicinity of R589 and D635 for W688X3-69 were recognized as an epitope. In addition, it was revealed that these amino acid residues recognized as an epitope were different from the amino acid residues thought to be important for the activity to hydrolyze FRETS-VWF73 and for the binding to VWF. It was suggested that the altered molecule having a reduced reactivity to antibodies from patients may be designed by this method without affecting the enzymatic activity through the epitope analysis of neutralizing antibodies from patients.

Example 8

Epitope Analysis of Neutralizing Antibody 2

Figure 7:
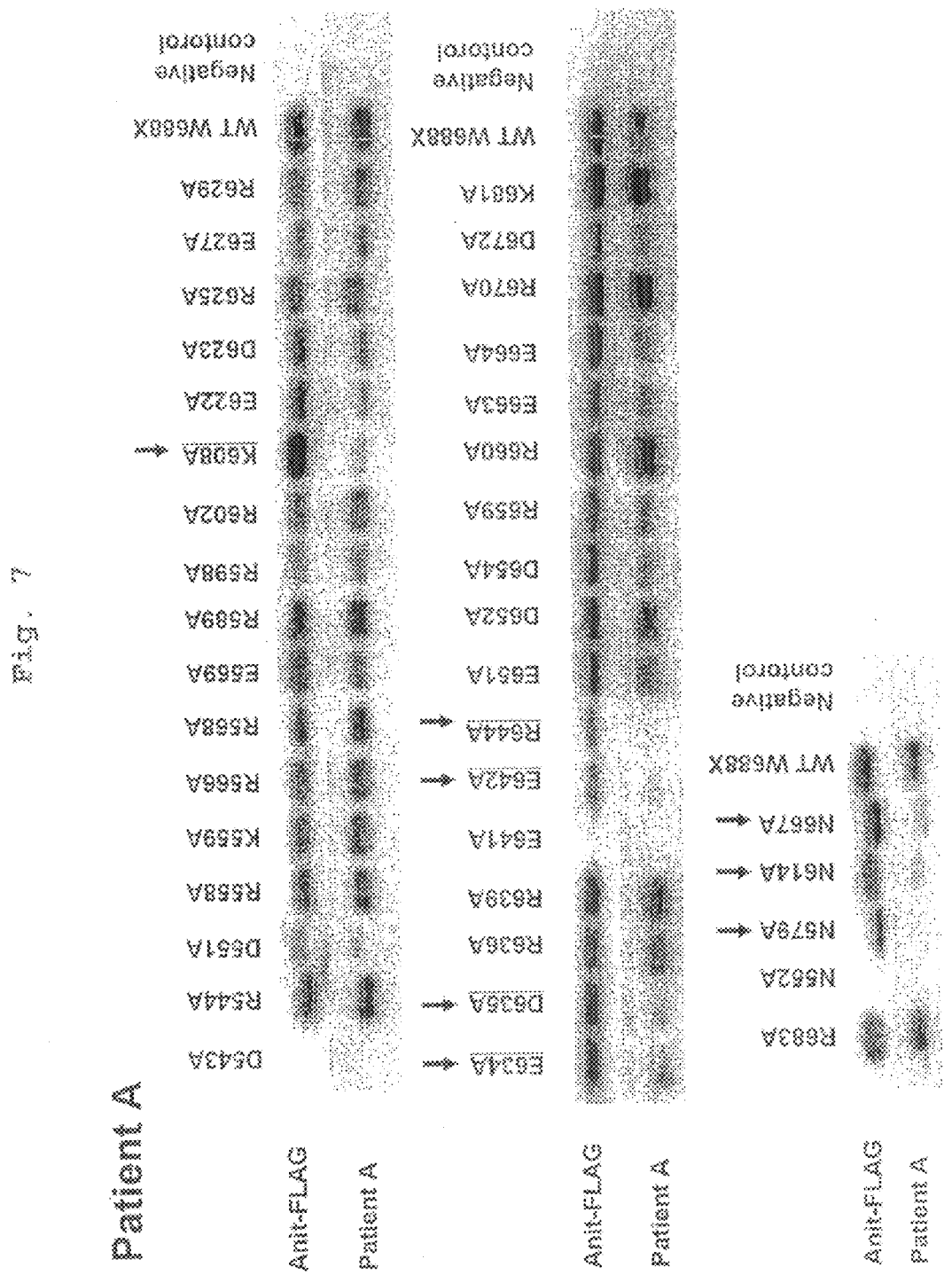
FIG. 7 shows the results of Western blot for an epitope analysis of an autoantibody of acquired TTP patient A. The arrows indicate the estimated epitope amino acids.
Figure 8:
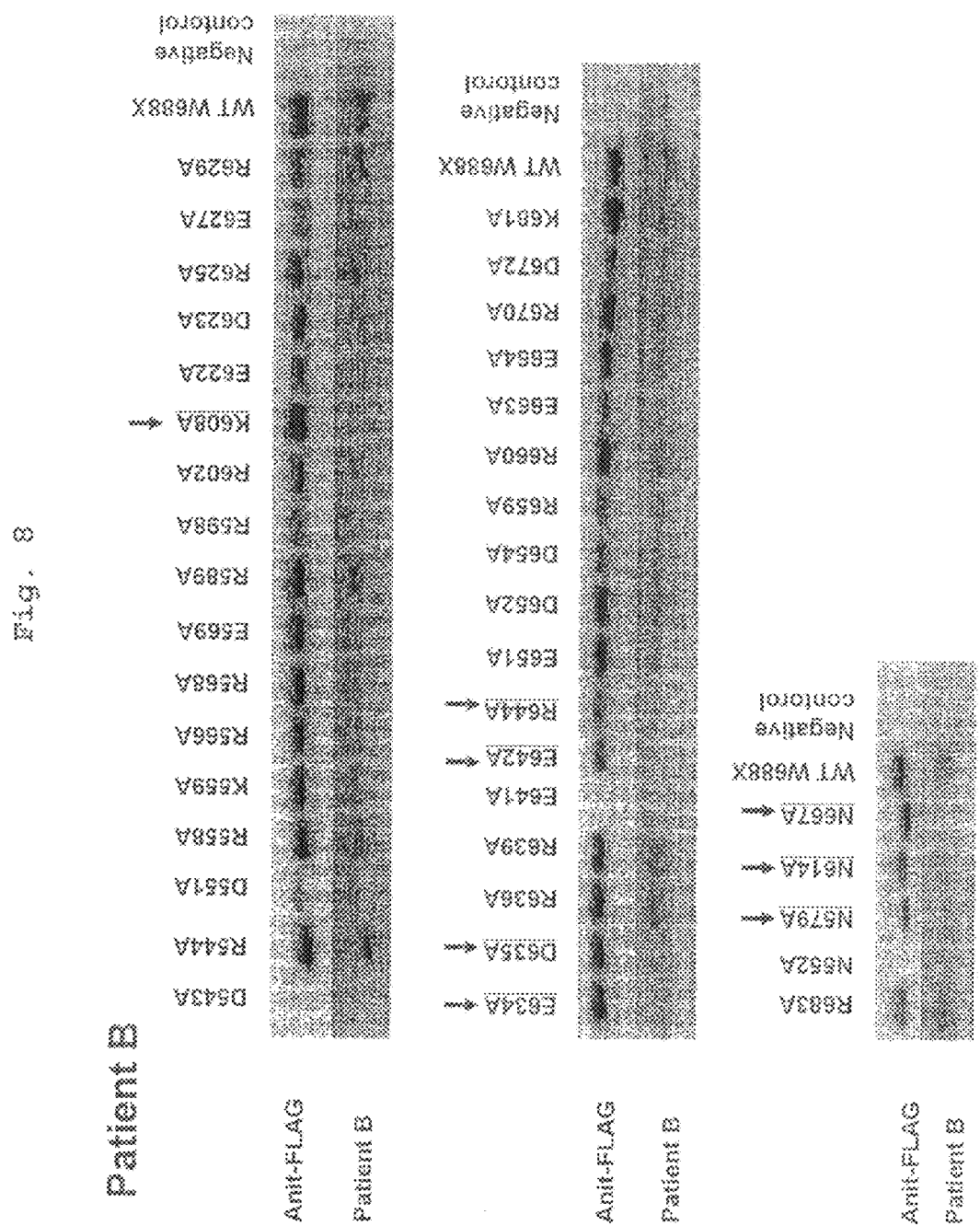
FIG. 8 shows the results of Western blot for an epitope analysis of an autoantibody of acquired TTP patient B. The arrows indicate the estimated epitope amino acids.
Figure 9:
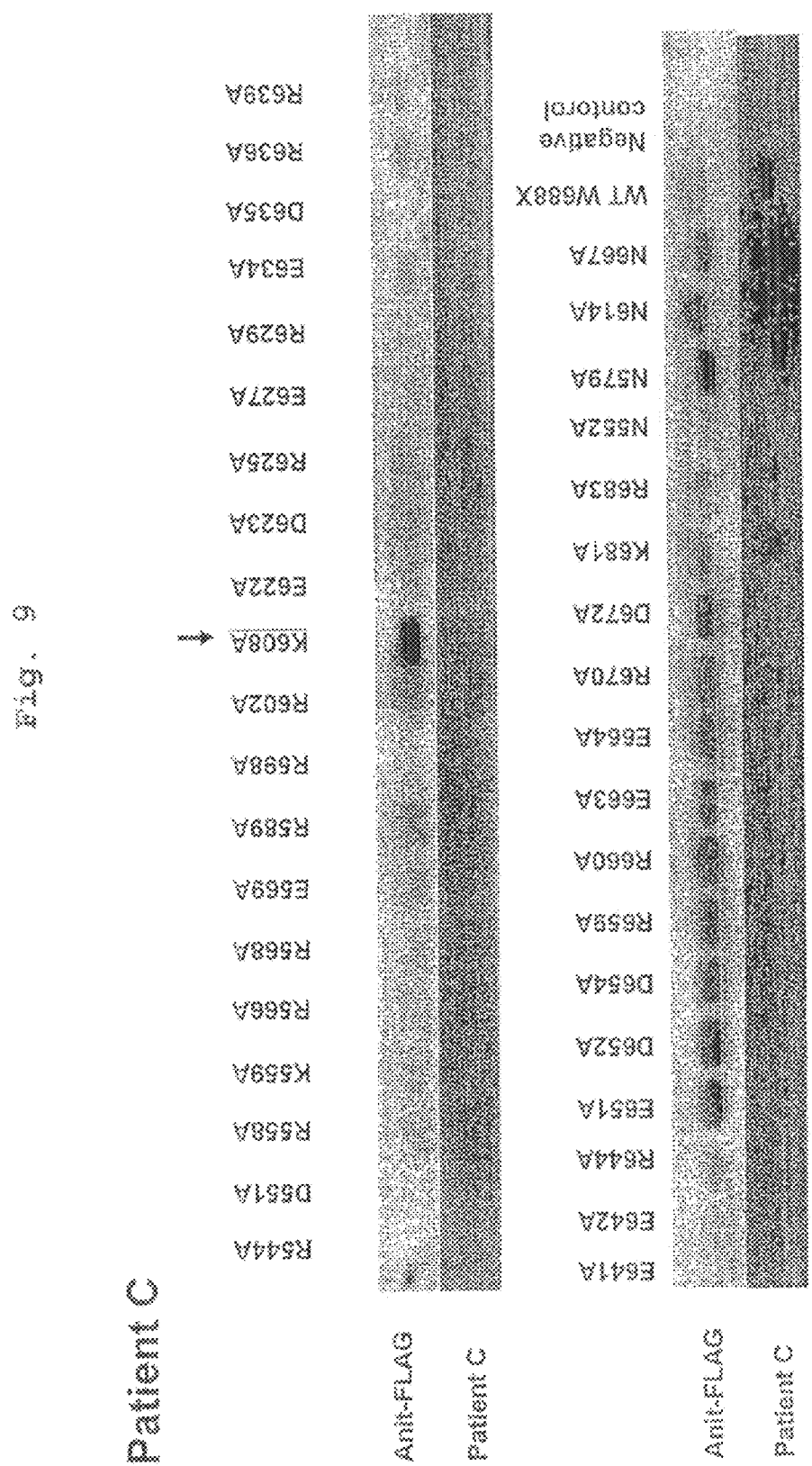
FIG. 9 shows the results of Western blot for an epitope analysis of an autoantibody of acquired TTP patient C. The arrows indicate the estimated epitope amino acids.

Following the WB (under non-reducing condition) to confirm the expression in Example 3, the anti-FLAG antibody was released with a WB releasing solution (NAKARAI), in a similar way to Example 7, reacted again with immunoglobulin G (IgG) fractions isolated from acquired TTP patients having the ability to neutralize the ADAMTS-13 activity, and visualized with an HRP labeled form of the anti-human immunoglobulin (Dako) wherein the epitopes of the antibodies were confirmed by a reduced color intensity (FIGS. 7 to 9). As a result, it was suggested that the vicinity of K608, E634, D635, E642 and R644 in the spacer domain and N578, N614 and N667 in the glycosylation site were recognized as an epitope. In addition, it was revealed that these amino acid residues recognized as an epitope were different from the amino acid residues thought to be important for the activity to hydrolyze FRETS-VWF73 and for the binding to VWF. Therefore, the substitution of these major epitope amino acids with different amino acids allows for preparing altered molecules having the reduced reactivity to antibodies from patients while the enzymatic activity is maintained or even enhanced like the mutant of E327.

Example 9

Evaluation of Mutants with Reduced Reactivities with Antibodies from Patients

Figure 10:
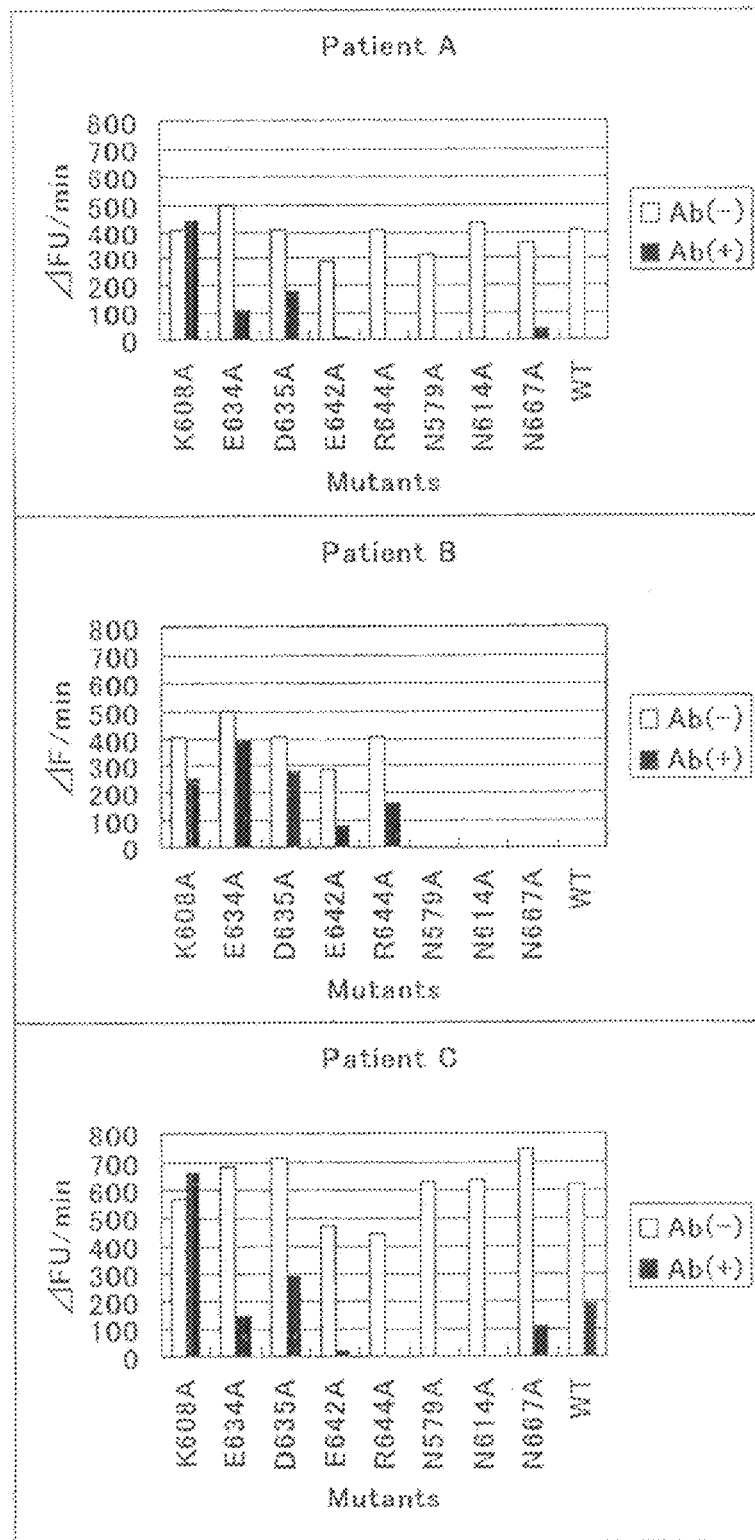
FIG. 10 shows evaluation of the cleaving activity of ADAMTS-13 mutant which has a reduced reactivity to an acquired TTP autoantibody to the synthetic substrate FRETS-VWF73.

The reactivity of the mutants, which were estimated from the result of Example 8 to have the reduced reactivity with autoantibodies from acquired TTP patients (K608A, E634A, D635A, E642A, R644A, and glycosylation site N578A, N614A, N667A), with the autoantibodies was evaluated using the commercially available fluorescent substrate FRETS-VWF73(PEPTIDE INSTITUTE, INC.) (FIG. 10). The cleaving activity of the ADAMTS-13 mutants to the FRETS-VWF73 fluorescent substrate per 1 min. (AFU/min) was measured with and without addition of antibodies from patients A, B and C (Ab+/−) to select mutants having a sufficient enzymatic activity even when a neutralizing antibody from the patients is added (i.e. the enzymatic activity kept at 500 or more of that of without addition of the neutralizing antibodies). As a result, it was revealed that depending on patient antibody, K608A, E634A and D635A had a sufficient enzymatic activity. In addition, K608A was revealed to have a sufficient enzymatic activity to all the patient antibodies.

Therefore, the substitution of these major epitope amino acids with different amino acids which reduce the antibody reactivity allows for preparing altered molecules (e.g. double mutant such as E327A/K608A) having the reduced reactivity to antibodies from patients while the enzymatic activity is maintained or even enhanced like the E327 mutant.

INDUSTRIAL APPLICABILITY

The ADAMTS-13 mutant of the present invention may be used as a medicament significantly efficacious as a supplemental treatment to thrombotic disease such as TTP.

SEQUENCE LISTING

```
<160> NUMBER OF SEQ ID NOS: 81

<210> SEQ ID NO 1
<211> LENGTH: 2088
<212> TYPE: DNA
<213> ORGANISM: Homo sapiens

<400> SEQUENCE: 1
atgcaccagc gtcaccccg ggcaagatgc cctcccctct gtgtggccgg aatccttgcc      60
tgtggctttc tcctgggctg ctggggaccc tcccattcc agcagagttg tcttcaggct     120
ttggagccac aggccgtgtc ttcttacttg agccctggtg ctcccttaaa aggccgccct     180
ccttcccctg gcttccagag gcagaggcag aggcagagac gggctgcagg cggcatccta     240
cacctggagc tgctggtggc cgtgggcccc gatgtcttcc aggctcacca ggaggacaca     300
```

-continued

```
gagcgctatg tgctcaccaa cctcaacatc ggggcagaac tgcttcggga cccgtccctg    360
ggggctcagt ttcgggtgca cctggtgaag atggtcattc tgacagagcc tgagggtgct    420
ccaaatatca cagccaacct cacctcgtcc ctgctgagcg tctgtgggtg gagccagacc    480
atcaaccctg aggacgacac ggatcctggc catgctgacc tggtcctcta tatcactagg    540
tttgacctgg agttgcctga tggtaaccgg caggtgcggg gcgtcaccca gctgggcggt    600
gcctgctccc caacctggag ctgcctcatt accgaggaca ctggtttcga cctgggagtc    660
accattgccc atgagattgg cacagcttc ggcctggagc acgacggcgc gcccggcagc    720
ggctgcggcc ccagcggaca cgtgatggct cggacggcg ccgcgcccg cgccggcctc    780 gcctggtccc cctgcagccg ccggcagctg ctgagcctgc tcagcgcagg acgggcgcgc    840
tgcgtgtggg acccgccgcg gcctcaaccc gggtccgcgg ggcacccgcc ggatgcgcag    900
cctggcctct actacagcgc caacgagcag tgccgcgtgg ccttcggccc caaggctgtc    960
gcctgcacct tcgccaggga gcacctggat atgtgccagg ccctctcctg ccacacagac   1020
ccgctggacc aaagcagctg cagccgcctc ctcgttcctc tcctggatgg gacagaatgt   1080
ggcgtggaga gtggtgctc caagggtcgc tgccgctccc tggtggagct gaccccata    1140 gcagcagtgc atgggcgctg gtctagctgg ggtccccgaa gtccttgctc ccgctcctgc   1200
ggaggaggtg tggtcaccag gaggcggcag tgcaacaacc ccagacctgc ctttggggg    1260 cgtgcatgtg ttggtgctga cctccaggcc gagatgtgca acactcaggc ctgcgagaag   1320
acccagctgg agttcatgtc gcaacagtgc gccaggaccg acggccagcc gctgcgctcc   1380 tccctggcg gcgcctcctt ctaccactgg ggtgctgctg taccacacag ccaaggggat   1440
gctctgtgca gacacatgtg ccgggccatt ggcgagagct tcatcatgaa gcgtggagac   1500
agcttcctcg atgggacccg gtgtatgcca agtggcccc ggggaggacgg gaccctgagc   1560 ctgtgtgtgt cggcagctg caggacattt ggctgtgatg gtaggatgga ctcccagcag   1620
gtatgggaca ggtgccaggt gtgtggtggg acaacagca cgtgcagccc acggaagggc   1680
tctttcacag ctggcagagc gagagaatat gtcacgtttc tgacagttac ccccaacctg   1740
accagtgtct acattgccaa ccacaggcct ctcttcacac acttggcggt gaggatcgga   1800
gggcgctatg tcgtggctgg gaagatgagc atctccccta acaccaccta cccctccctc   1860
ctggaggatg tcgtgtcga gtacagagtg gccctcaccg aggaccggct gccccgcctg   1920
gaggagatcc gcatctgggg accccctccag gaagatgctg acatccaggt ttacaggcgg   1980
tatggcgagg agtatggcaa cctcacccgc ccagacatca ccttcaccta cttccagcct   2040
aagccacggc aggcctgggt ggactacaag gacgatgacg ataagtga              2088
```

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
primer which is used to genetically change the 287th Arg of
ADAMTS-13 to Ala

<400> SEQUENCE: 2
gacccgccgg cgcctcaacc c    21

<210> SEQ ID NO 3
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer which is used to genetically change the 298th Asp of
      ADAMTS-13 to Ala

<400> SEQUENCE: 3
cacccgccgg ctgcgcagcc                                                   20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 309th Glu of
      ADAMTS-13 to Ala

<400> SEQUENCE: 4
agcgccaacg cgcagtgccg c                                                 21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 312th Arg of
      ADAMTS-13 to Ala

<400> SEQUENCE: 5
gagcagtgcg ccgtggcctt c                                                 21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 318th Lys of
      ADAMTS-13 to Ala

<400> SEQUENCE: 6
ttcggccccg cggctgtcgc c                                                 21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 326th Arg of
      ADAMTS-13 to Ala

<400> SEQUENCE: 7
accttcgccg cggagcacct g                                                 21

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer which is used to genetically change the 327th Glu of
      ADAMTS-13 to Ala

<400> SEQUENCE: 8
ttcgccaggg cgcacctgg                                                    19
```

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
    primer which is used to genetically change the 330th Asp of
    ADAMTS-13 to Ala

<400> SEQUENCE: 9
gagcacctgg ctatgtgcca g                                      21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
    primer which is used to genetically change the 340th Asp of
    ADAMTS-13 to Ala

<400> SEQUENCE: 10
tgccacacag ccccgctgga c                                      21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
    primer which is used to genetically change the 343th Asp of
    ADAMTS-13 to Ala

<400> SEQUENCE: 11
gacccgctgg cccaaagcag c                                      21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
    primer which is used to genetically change the 349th Arg of
    ADAMTS-13 to Ala

<400> SEQUENCE: 12
agctgcagcg ccctcctcgt tc                                     22

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
    primer which is used to genetically change the 356th Asp of
    ADAMTS-13 to Ala

<400> SEQUENCE: 13
cctctcctgg ctgggacaga atg                                    23

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
    primer which is used to genetically change the 359th Glu of ADAMTS-13 to Ala

<400> SEQUENCE: 14
gatgggacag catgtggcgt g                                          21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 363th Glu of
      ADAMTS-13 to Ala

<400> SEQUENCE: 15
tgtggcgtgg cgaagtggtg c                                          21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 364th Lys of
      ADAMTS-13 to Ala

<400> SEQUENCE: 16
ggcgtggagg cgtggtgctc c                                          21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 368th Lys of
      ADAMTS-13 to Ala

<400> SEQUENCE: 17
tggtgctccg cgggtcgctg c                                          21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 370th Arg of
      ADAMTS-13 to Ala

<400> SEQUENCE: 18
tccaagggtg cctgccgctc c                                          21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 372th Arg of
      ADAMTS-13 to Ala

<400> SEQUENCE: 19
ggtcgctgcg cctccctggt g                                          21

<210> SEQ ID NO 20
<211> LENGTH: 21

-continued

```
<212> TYPE: DNA
<213> ORGANISM: Artificial Sequence
<220> FEATURE:
<223> OTHER INFORMATION: Description of Artificial Sequence: Synthetic
      primer which is used to genetically change the 376th Glu of
      ADAMTS-13 to Ala

<400> SEQUENCE: 20
tccctggtgg cgctgacccc c                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 386th Arg of
      ADAMTS-13 to Ala

<400> SEQUENCE: 21
gtgcatgggg cctggtctag c                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 452th Arg of
      ADAMTS-13 to Ala

<400> SEQUENCE: 22
cagtgcgccg cgaccgacgg c                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 454th Asp of
      ADAMTS-13 to Ala

<400> SEQUENCE: 23
gccaggaccg ccggccagcc g                                              21

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer which is used to genetically change the 459th Arg of
      ADAMTS-13 to Ala

<400> SEQUENCE: 24
cagccgctgg cctcctcccc tg                                             22

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 480th Asp of
      ADAMTS-13 to Ala

<400> SEQUENCE: 25
```
agccaagggg ctgctctgtg c                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 484th Arg of
      ADAMTS-13 to Ala

<400> SEQUENCE: 26
gctctgtgcg cacacatgtg c                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 488th Arg of
      ADAMTS-13 to Ala

<400> SEQUENCE: 27
cacatgtgcg cggccattgg c                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 492th Glu of
      ADAMTS-13 to Ala

<400> SEQUENCE: 28
gccattggcg cgagcttcat c                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 497th Lys of
      ADAMTS-13 to Ala

<400> SEQUENCE: 29
ttcatcatgg cgcgtggaga c                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 498th Arg of
      ADAMTS-13 to Ala

<400> SEQUENCE: 30
atcatgaagg ctggagacag c                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic primer which is used to genetically change the 500th Asp of
ADAMTS-13 to Ala

<400> SEQUENCE: 31
aagcgtggag ccagcttcct c                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 504th Asp of
      ADAMTS-13 to Ala

<400> SEQUENCE: 32
agcttcctcg ctgggacccg g                                              21

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer which is used to genetically change the 507th Arg of
      ADAMTS-13 to Ala

<400> SEQUENCE: 33
gatgggaccg cgtgtatgcc                                                20

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 514th Arg of
      ADAMTS-13 to Ala

<400> SEQUENCE: 34
agtggccccg cggaggacgg g                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 515th Glu of
      ADAMTS-13 to Ala

<400> SEQUENCE: 35
ggcccccggg cggacgggac c                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 516th Asp of
      ADAMTS-13 to Ala

<400> SEQUENCE: 36
ccccgggagg ccgggaccct g                                              21

<210> SEQ ID NO 37

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 528th Arg of
      ADAMTS-13 to Ala

<400> SEQUENCE: 37
ggcagctgcg cgacatttgg c                                             21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 533th Asp of
      ADAMTS-13 to Ala

<400> SEQUENCE: 38
tttggctgtg ctggtaggat g                                             21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 535th Arg of
      ADAMTS-13 to Ala

<400> SEQUENCE: 39
tgtgatggtg cgatggactc c                                             21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 537th Asp of
      ADAMTS-13 to Ala

<400> SEQUENCE: 40
ggtaggatgg cctcccagca g                                             21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 543th Asp of
      ADAMTS-13 to Ala

<400> SEQUENCE: 41
caggtatggg ccaggtgcca g                                             21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 544th Arg of
      ADAMTS-13 to Ala

<400> SEQUENCE: 42
```

-continued gtatgggacg cgtgccaggt g                                          21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 551th Asp of
      ADAMTS-13 to Ala

<400> SEQUENCE: 43
tgtggtgggg ccaacagcac g                                          21

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer which is used to genetically change the 558th Arg of
      ADAMTS-13 to Ala

<400> SEQUENCE: 44
tgcagcccag cgaagggctc                                            20

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 559th Lys of
      ADAMTS-13 to Ala

<400> SEQUENCE: 45
agcccacggg cgggctcttt c                                          21

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      primer which is used to genetically change the 566th Arg of
      ADAMTS-13 to Ala

<400> SEQUENCE: 46
acagctggcg cagcgagag                                             19

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 568th Arg of
      ADAMTS-13 to Ala

<400> SEQUENCE: 47
ggcagagcgg cagaatatgt c                                          21

<210> SEQ ID NO 48
<211> LENGTH: 21
<212> TYPE: DNA
<213> ORGANISM: Artificial Sequence
<220> FEATURE:

```
<223> OTHER INFORMATION: Description of Artificial Sequence: Synthetic
      primer which is used to genetically change the 569th Glu of
      ADAMTS-13 to Ala

<400> SEQUENCE: 48
agagcgagag catatgtcac g                                              21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 589th Arg of
      ADAMTS-13 to Ala

<400> SEQUENCE: 49
gccaaccacg cgcctctctt c                                              21

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer which is used to genetically change the 598th Arg of
      ADAMTS-13 to Ala

<400> SEQUENCE: 50
ttggcggtgg cgatcggagg                                                20

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 602th Arg of
      ADAMTS-13 to Ala

<400> SEQUENCE: 51
atcggagggg cctatgtcgt g                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 608th Lys of
      ADAMTS-13 to Ala

<400> SEQUENCE: 52
gtggctgggg cgatgagcat c                                              21

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer which is used to genetically change the 622th Glu of
      ADAMTS-13 to Ala

<400> SEQUENCE: 53
tccctcctgg cggatggtcg                                                20
```

```
<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 623th Asp of
      ADAMTS-13 to Ala

<400> SEQUENCE: 54
ctcctggagg ctggtcgtgt c                                              21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 625th Arg of
      ADAMTS-13 to Ala

<400> SEQUENCE: 55
gaggatggtg ctgtcgagta c                                              21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 627th Glu of
      ADAMTS-13 to Ala

<400> SEQUENCE: 56
ggtcgtgtcg cgtacagagt g                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 629th Arg of
      ADAMTS-13 to Ala

<400> SEQUENCE: 57
gtcgagtacg cagtggccct c                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 634th Glu of
      ADAMTS-13 to Ala

<400> SEQUENCE: 58
gccctcaccg cggaccggct g                                              21

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer which is used to genetically change the 635th Asp of
      ADAMTS-13 to Ala
```

<400> SEQUENCE: 59
ctcaccgagg cccggctgcc 20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
    primer which is used to genetically change the 636th Arg of
    ADAMTS-13 to Ala

<400> SEQUENCE: 60
accgaggacg cgctgccccg 20

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
    primer which is used to genetically change the 639th Arg of
    ADAMTS-13 to Ala

<400> SEQUENCE: 61
cggctgcccg ccctggagga g 21

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
    primer which is used to genetically change the 641th Glu of
    ADAMTS-13 to Ala

<400> SEQUENCE: 62
ccccgcctgg cggagatccg 20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
    primer which is used to genetically change the 642th Glu of
    ADAMTS-13 to Ala

<400> SEQUENCE: 63
cgcctggagg cgatccgcac 20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
    primer which is used to genetically change the 644th Arg of
    ADAMTS-13 to Ala

<400> SEQUENCE: 64
gaggagatcg ccatctgggg 20

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 651th Glu of
      ADAMTS-13 to Ala

<400> SEQUENCE: 65
cccctccagg cagatgctga c                                           21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 652th Asp of
      ADAMTS-13 to Ala

<400> SEQUENCE: 66
ctccaggaag ctgctgacat c                                           21

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence: Synthetic
      primer which is used to genetically change the 654th Asp of
      ADAMTS-13 to Ala

<400> SEQUENCE: 67
gaagatgctg ccatccagg                                              19

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer which is used to genetically change the 659th Arg of
      ADAMTS-13 to Ala

<400> SEQUENCE: 68
caggtttacg cgcggtatgg                                             20

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 660th Arg of
      ADAMTS-13 to Ala

<400> SEQUENCE: 69
gtttacaggg cgtatggcga g                                           21

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer which is used to genetically change the 663th Glu of
      ADAMTS-13 to Ala

<400> SEQUENCE: 70
cggtatggcg cggagtatgg                                             20

-continued

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 664th Glu of
      ADAMTS-13 to Ala

<400> SEQUENCE: 71
tatggcgagg cgtatggcaa c                                              21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 670th Arg of
      ADAMTS-13 to Ala

<400> SEQUENCE: 72
aacctcaccg ccccagacat c                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 672th Asp of
      ADAMTS-13 to Ala

<400> SEQUENCE: 73
acccgcccag ccatcacctt c                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 681th Lys of
      ADAMTS-13 to Ala

<400> SEQUENCE: 74
ttccagcctg cgccacggca g                                              21

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer which is used to genetically change the 683th Arg of
      ADAMTS-13 to Ala

<400> SEQUENCE: 75
cctaagccag cgcaggcctg                                                20

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 552th Asn of
      ADAMTS-13 to Ala

<400> SEQUENCE: 76
ggtggggacg ccagcacgtg c                                              21

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer which is used to genetically change the 579th Asn of
      ADAMTS-13 to Ala

<400> SEQUENCE: 77 gttaccccg ccctgaccag                                                 20

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 614th Asn of
      ADAMTS-13 to Ala

<400> SEQUENCE: 78
atctcccctg ccaccaccta c                                              21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      primer which is used to genetically change the 667th Asn of
      ADAMTS-13 to Ala

<400> SEQUENCE: 79
gagtatggcg ccctcacccg c                                              21

<210> SEQ ID NO 80
<211> LENGTH: 4
<212> TYPE: PRT
<213> ORGANISM: Homo sapiens

<400> SEQUENCE: 80

Arg Gln Arg Arg
1

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      primer consensus sequence
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (6)..(7)
<223> OTHER INFORMATION: Any amino acid
<220> FEATURE:
<221> NAME/KEY: MOD_RES
<222> LOCATION: (9)..(10)
<223> OTHER INFORMATION: Any amino acid

```
<400> SEQUENCE: 81

His Glu Xaa Xaa His Xaa Xaa Gly Xaa Xaa His Asp
1               5                   10
```

The invention claimed is:

1. An ADAMTS-13 (a disintegrin-like domain, and metalloprotease, with an isolated human thrombospondin type 1 motif, member 13) mutant, comprising a substitution of the following positions in the isolated human ADAMTS-13 with a different amino acid: aspartic acid at position 287, aspartic acid at position 298, glutamic acid at position 309, arginine at position 312, lysine at position 318, glutamic acid at position 327, aspartic acid at position 340, glutamic acid at position 363, lysine at position 364, lysine at position 368, arginine at position 370, arginine at position 372, arginine at position 386, arginine at position 452, arginine at position 459, glutamic acid at position 492, lysine at position 497, aspartic acid at position 500, aspartic acid at position 504, arginine at position 514, glutamic acid at position 515, aspartic acid at position 516, arginine at position 535, aspartic acid at position 537, arginine at position 544, aspartic acid at position 551, asparagine at position 552, arginine at position 558, lysine at position 559, arginine at position 566, arginine at position 568, glutamic acid at position 569, asparagine at position 579, lysine at position 608, asparagine at position 614, arginine at position 625, arginine at position 629, glutamic acid at position 634, aspartic acid at position 635, arginine at position 636, arginine at position 639, arginine at position 644, glutamic acid at position 651, arginine at position 659, glutamic acid at position 663, glutamic acid at position 664, asparagine at position 667, arginine at position 670, or arginine at position 683 in the amino acid sequence encoded by the nucleotide sequence of SEQ ID NO:1.

2. The ADAMTS-13 mutant according to claim 1, comprising a substitution of arginine at position 312, lysine at position 318, arginine at position 568, glutamic acid at position 569, asparagine at position 579, lysine at position 608, asparagine at position 614, glutamic acid at position 634, aspartic acid at position 635 or arginine at position 639, glutamic acid at position 644, or asparagine at position 667.

3. The ADAMTS-13 mutant according to claim 1, comprising a substitution of arginine at position 312, lysine at position 318, arginine at position 568, glutamic acid at position 569, asparagine at position 579, lysine at position 608, asparagine at position 614, glutamic acid at position 634, aspartic acid at position 635, arginine at position 639, arginine at position 644, glutamic acid at position 651, arginine at position 659, glutamic acid at position 663, glutamic acid at position 664, asparagine at position 667, or arginine at position 670.

4. The ADAMTS-13 mutant according to claim 1, wherein the different amino acid is an uncharged amino acid.

5. The ADAMTS-13 mutant according to claim 2, wherein the different amino acid is an uncharged amino acid.

6. The ADAMTS-13 mutant according to claim 3, wherein the different amino acid is an uncharged amino acid.

7. The ADAMTS-13 mutant according to claim 4, wherein the uncharged amino acid is selected from the group consisting of alanine, glycine, proline, serine and threonine.

8. The ADAMTS-13 mutant according to claim 5, wherein the uncharged amino acid is selected from the group consisting of alanine, glycine, proline, serine and threonine.

9. The ADAMTS-13 mutant according to claim 6, wherein the uncharged amino acid is selected from the group consisting of alanine, glycine, proline, serine and threonine.

* * * * *